(12) United States Patent
Brown, III

(10) Patent No.: US 12,150,554 B2
(45) Date of Patent: Nov. 26, 2024

(54) PILLOW SLEEVE DEVICE, SYSTEM, AND METHOD

(71) Applicant: JAY INNOVATIONS LLC, Lakeland, FL (US)

(72) Inventor: Joseph Wesley Brown, III, Lakeland, FL (US)

(73) Assignee: JAY INNOVATIONS LLC, Lakeland, FL (US)

(*) Notice: Subject to any disclaimer, the term of this patent is extended or adjusted under 35 U.S.C. 154(b) by 0 days.

(21) Appl. No.: 18/497,116

(22) Filed: Oct. 30, 2023

(65) Prior Publication Data

US 2024/0306823 A1  Sep. 19, 2024

Related U.S. Application Data

(60) Provisional application No. 63/452,354, filed on Mar. 15, 2023.

(51) Int. Cl.
*A47C 16/00* (2006.01)
*A61M 21/00* (2006.01)

(52) U.S. Cl.
CPC ............ *A47C 16/00* (2013.01); *A61M 21/00* (2013.01); *A61M 2021/0022* (2013.01);
(Continued)

(58) Field of Classification Search
CPC .................. A47C 16/00; A61M 21/00; A61M 2021/0022; A61M 2021/0027;
(Continued)

(56) References Cited

U.S. PATENT DOCUMENTS 4,465,064 A * 8/1984 Boone ...................... A61D 9/00
602/12
4,927,025 A * 5/1990 Thompson ............ A61F 15/004
206/223
(Continued)

FOREIGN PATENT DOCUMENTS

CN        115177841 A      10/2022
WO  WO-2012076996 A1 *  6/2012  ............ A41D 1/205
WO     2023022989 A1      2/2023

OTHER PUBLICATIONS

E.D.W. Lynch, "Ostrich Pillow Mini, a Wearable Pillow That Turns Your Hand or Arm Into a Soft Cushion for Your Head", webpage, Oct. 13, 2014, https://laughingsquid.com/ostrich-pillow-mini/.
(Continued)

*Primary Examiner* — Myles A Throop
(74) *Attorney, Agent, or Firm* — Jacob M. Ward; Ward Law Office LLC

(57) ABSTRACT

A pillow sleeve device that slips over the arm of the user and allows the user to rest or sleep on it is disclosed. The pillow sleeve device improves on known pillows by being very lightweight and portable, being ambidextrous and usable on both arms, and by covering an entire forearm instead of just a portion of the arm under the pillow. The pillow sleeve can include a main body having an arm portion and a hand portion. The arm portion can be disposed proximal a first end of the main body and the hand portion can be disposed proximal a second end of the main body. The main body can include a hollow passage between the first end and the second end. The hand portion can include a thumb opening configured for receiving the thumb of the user.

19 Claims, 21 Drawing Sheets

(52) U.S. Cl.
CPC ............... *A61M 2021/0027* (2013.01); *A61M 2021/0044* (2013.01); *A61M 2021/0083* (2013.01)

(58) Field of Classification Search
CPC .. A61M 2021/0044; A61M 2021/0083; A41D 13/08
USPC ............................................................ 5/940
See application file for complete search history.

(56) References Cited

U.S. PATENT DOCUMENTS

| | | | | |
|---|---|---|---|---|
| D395,087 | S * | 6/1998 | Devries | D24/190 |
| 6,560,802 | B2 * | 5/2003 | Fujii | A63H 3/003 |
| | | | | 5/639 |
| D484,604 | S * | 12/2003 | Tramel | D24/190 |
| 6,808,501 | B2 * | 10/2004 | Stess | A61F 13/04 |
| | | | | 602/5 |
| 7,066,899 | B2 * | 6/2006 | Baron | A61F 13/041 |
| | | | | 602/3 |
| 7,299,685 | B1 | 11/2007 | Burnett | |
| 7,314,457 | B2 * | 1/2008 | Reaux | A61F 13/04 |
| | | | | 602/61 |
| 8,343,293 | B2 * | 1/2013 | Wood | B29C 63/40 |
| | | | | 156/86 |
| 10,716,418 | B2 | 7/2020 | Jaramillo | |
| 10,835,062 | B1 | 11/2020 | Calton | |
| D919,229 | S | 5/2021 | Bryngelson | |
| 2009/0053451 | A1 * | 2/2009 | Smith | B44C 1/1712 |
| | | | | 156/289 |
| 2009/0126068 | A1 | 5/2009 | Van Trojen | |
| 2009/0222993 | A1 | 9/2009 | Villanueva et al. | |
| 2013/0025060 | A1 | 1/2013 | Shull et al. | |
| 2014/0366273 | A1 | 12/2014 | Trent et al. | |
| 2017/0020738 | A1 * | 1/2017 | Jones | A61F 13/04 |
| 2017/0290450 | A1 * | 10/2017 | Jaramillo | A47C 7/383 |
| 2018/0242750 | A1 | 8/2018 | Wilson | |
| 2020/0253300 | A1 | 8/2020 | Redman | |
| 2021/0106155 | A1 * | 4/2021 | Sutton | A47G 9/1045 |
| 2022/0354281 | A1 | 11/2022 | Thompson et al. | |

OTHER PUBLICATIONS

Sleepy Sleeve, "Sleepy Sleeve—Wearable Arm Pillow", webpage, https://www.thegreenhead.com/2022/06/sleepy-sleeve-wearable-arm-pillow.php.
Written Opinion of the International Searching Authority dated Apr. 4, 2024.

* cited by examiner pillow sleeve device 100 main body 102 arm portion 126 forearm portion 146 flared forearm surface 148 forearm flare axis 150 forearm flare angle 152 maximum forearm portion length 147 maximum arm portion exterior diameter 141 hand portion 128 maximum hand portion exterior diameter 142 maximum hand portion length 144 wrist portion 130 flared wrist surface 154 wrist flare axis 156 wrist flare angle 158 maximum wrist portion exterior diameter 145

*FIG. 1B* pillow sleeve device 100
- main body 102
  - arm portion 126
    - forearm portion 146
      - flared forearm surface 148
      - forearm flare axis 150
      - forearm flare angle 152
      - maximum forearm portion length 147
      - maximum arm portion exterior diameter 141
    - hand portion 128
      - maximum hand portion exterior diameter 142
      - maximum hand portion length 144
  - wrist portion 130
    - flared wrist surface 154
    - wrist flare axis 156
    - wrist flare angle 158
    - maximum wrist portion exterior diameter 145
  - elbow portion 202
    - elbow portion axis 204
    - bend 206
    - elbow portion angle 208

*FIG. 2B* pillow sleeve device 100 main body 102 arm portion 126 forearm portion 146 flared forearm surface 148 forearm flare axis 150 forearm flare angle 152 maximum forearm portion length 147 maximum arm portion exterior diameter 141 hand portion 128 maximum hand portion exterior diameter 142 maximum hand portion length 144 wrist portion 130 flared wrist surface 154 wrist flare axis 156 wrist flare angle 158 maximum wrist portion exterior diameter 145

*FIG. 3B* pillow sleeve device 100 main body 102 arm portion 126 forearm portion 146 flared forearm surface 148 forearm flare axis 150 forearm flare angle 152 maximum forearm portion length 147 maximum arm portion exterior diameter 141 hand portion 128 maximum hand portion exterior diameter 142 maximum hand portion length 144 wrist portion 130 flared wrist surface 154 wrist flare axis 156 wrist flare angle 158 maximum wrist portion exterior diameter 145

*FIG. 4B* pillow sleeve device 100 main body 102 flexible shell 104 pouch 200 electronics package 600 power source 602 controller 604 visual unit 606
- light 608 auditory unit 610
- speaker 612 vibratory unit 614 user interface 616 transceiver 618 cushion fill 106 first end 108 hollow passage 112 second end 110 arm opening 114
- substantially round shape 132
- maximum arm opening interior diameter 138 other electronic device 620

*FIG. 6A*

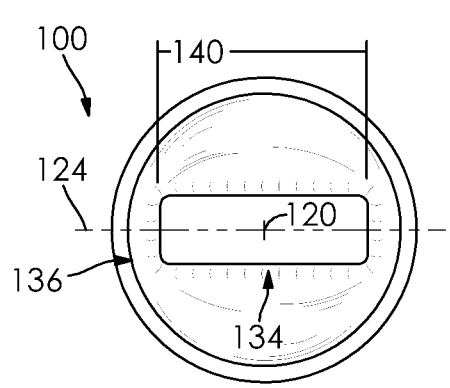
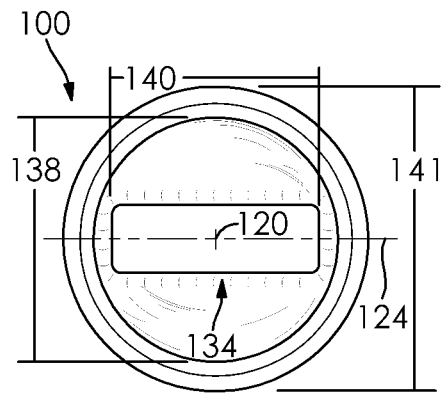
FIG. 12   FIG. 13
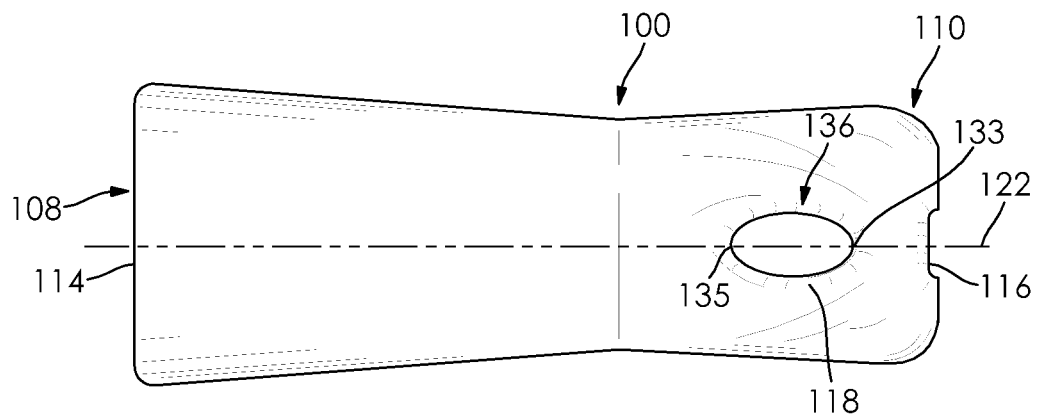
FIG. 14
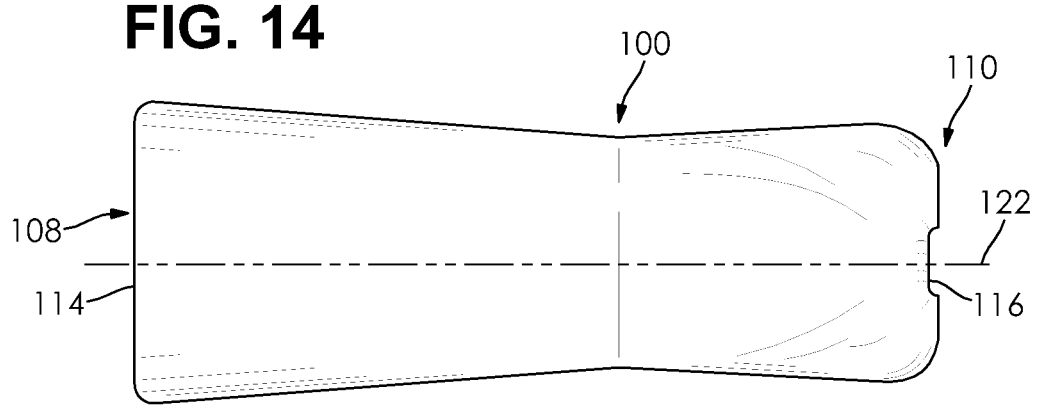
FIG. 15

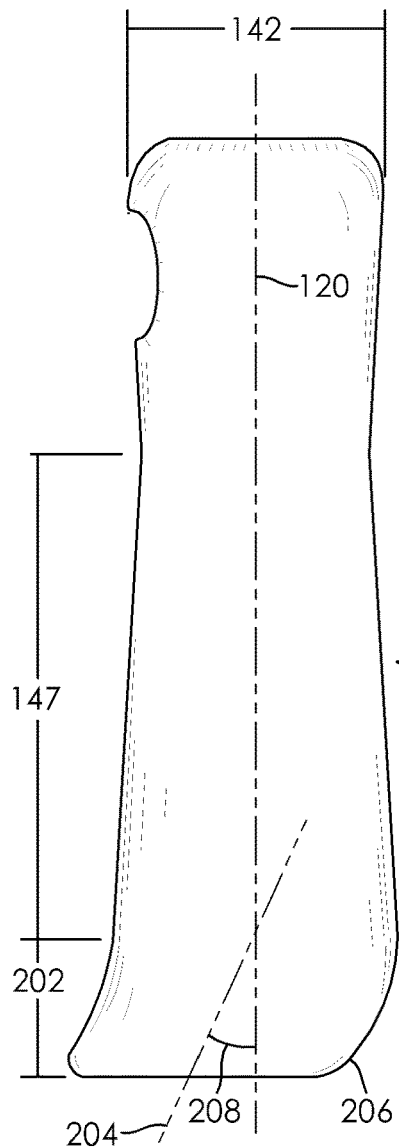
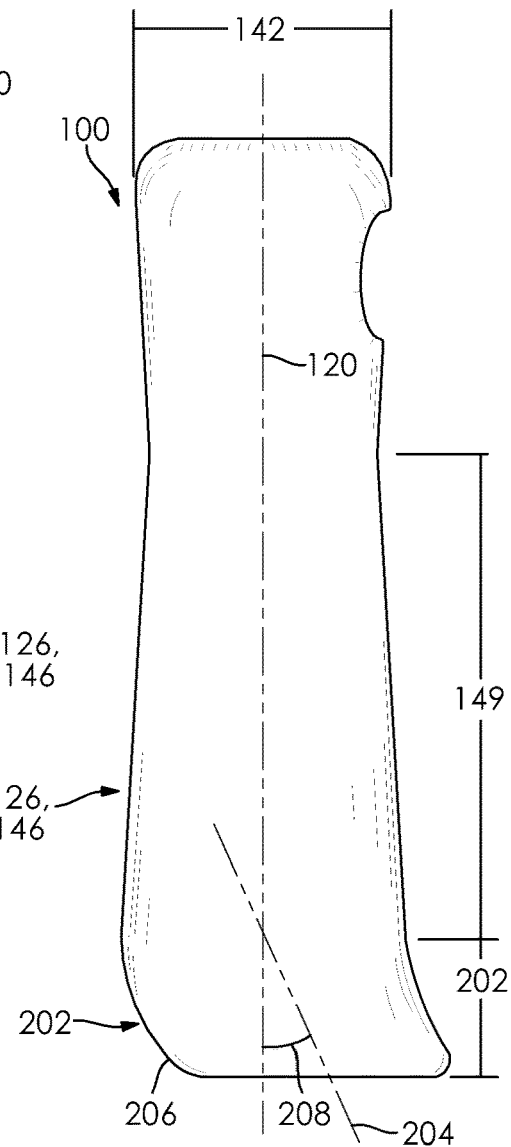
FIG. 18  FIG. 19
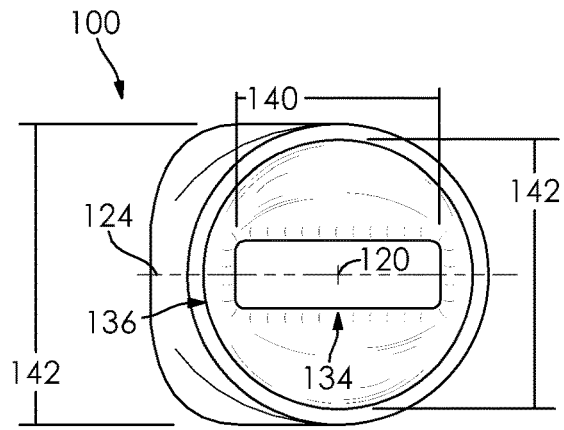
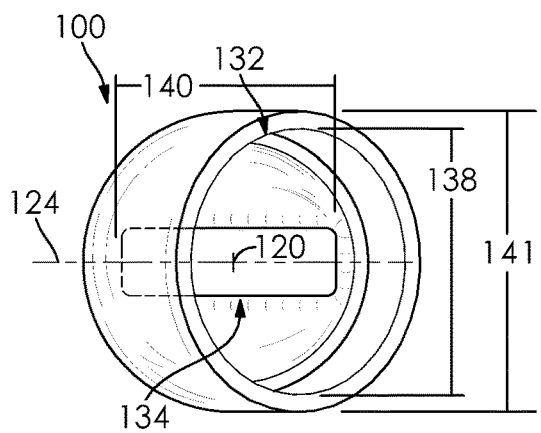
FIG. 20  FIG. 21

PILLOW SLEEVE DEVICE, SYSTEM, AND METHOD

CROSS REFERENCE TO RELATED APPLICATIONS

This application claims the benefit of U.S. Provisional Application No. 63/452,354 filed on Mar. 15, 2023. The entire disclosure of the above application is hereby incorporated herein by reference.

FIELD

The present technology relates to pillow accessories and, more specifically, to a pillow sleeve, an associated system, and methods designed to provide comfort and support for the arm of a user during rest or sleep.

INTRODUCTION

This section provides background information related to the present disclosure which is not necessarily prior art.

Traditional pillows often fail to adequately support the arm, leading to discomfort and potential sleep disturbances. Previous approaches to providing comfort and support for sleeping have involved various types of pillows and pillow accessories. Traditional pillows are typically rectangular in shape and are designed to support the head and neck while sleeping. However, these pillows do not provide support or padding for other parts of the body, such as the arm.

Some existing solutions include arm pillows or armrests that are separate from the main pillow. These arm pillows are typically designed to be placed next to the main pillow and provide a padded surface for the arm to rest on while sleeping. However, these arm pillows are not integrated with the main pillow and may shift or move during sleep, reducing their effectiveness in providing continuous support.

Other approaches involve the use of sleeves or wraps that are designed to be worn on the arm while sleeping. These sleeves are typically made of fabric and provide a padded surface for the arm. However, these sleeves do not provide the same level of support and comfort as a pillow, as they do not have sufficient cushioning materials.

Additionally, some existing solutions include fingerless gloves or wrist pads that are designed to provide support and comfort for the hand and wrist. However, these fingerless gloves are not integrated with the arm pillow or sleeve and may not provide the desired level of support and comfort for the entire arm.

Various pillow accessories have also been developed to address these problems, including pillow sleeves. One known pillow accessory is described in U.S. Pat. No. 10,835,062 to Calton. The pillow accessory of Calton is directed to an ergonomic pillow sleeve having a fabric layer and a memory foam layer, which provides a padded surface for sleeping. The Claton pillow accessory is also designed to wrap entirely around the arm of a user, extending from the hand to the shoulder. The Calton pillow accessory includes a fingerless glove with an under-wrist pad and a palm wrist pad for added comfort and support. Additionally, the pillow sleeve device of Calton has a flap that is connected to the sleeve, and which allows the user to adjust the tightness of the sleeve by manipulating hook and loop tape connections. Furthermore, the Calton pillow sleeve device has an elbow pad that is provided on either the sleeve or the flap, enhancing overall comfort and support.

Nonetheless, these known pillow sleeves like Calton often lack flexibility and customizability, limiting their effectiveness in providing personalized comfort and support. Such previous approaches to providing comfort have not sufficiently provided a comprehensive solution that meets the needs and desires of most users.

There is a continuing need for a pillow sleeve device having a customizable soft surface in combination with openings to slip a hand and fingers therethrough. Desirably, the pillow sleeve device is lightweight, durable, machine washable, usable on either arm, and can easily fit inside of conventional backpacks or suitcases.

SUMMARY

In concordance with the instant disclosure, a pillow sleeve device having a customizable soft surface in combination with openings to slip a hand and fingers therethrough, and which is lightweight, durable, machine washable, usable on either arm, and can easily fit inside of conventional backpacks or suitcases, has been surprisingly discovered.

The present technology includes articles of manufacture, systems, and processes that relate to pillow sleeves and related devices.

In one embodiment, a pillow sleeve device has a main body including at least one flexible shell and at least one cushion fill. The at least one flexible shell envelopes the at least one cushion fill. The at least one flexible shell and the at least one cushion fill together provide a soft resting surface for sleeping or resting by a user. The main body further has a first end, a second end, and a hollow passage. The hollow passage is disposed between the first end and the second end. The main body also has an arm opening, a fingers opening, and a thumb opening. The arm opening is in communication with the fingers opening by the hollow passage of the main body. The main body including the hollow passage is elongate and is generally arranged on a central axis. The main body of the pillow sleeve device further has an arm portion and a hand portion.

The arm portion with the arm opening of the main body is configured to receive and be supported by at least part of an arm of the user. The hand portion is configured to receive and be supported by at least part of a hand of the user. The arm portion is disposed proximal the first end of the main body, and the hand portion is disposed proximal the second end of the main body. The arm portion with the arm opening is configured to receive the hand and the arm during a wearing of the pillow sleeve device by the user. The hand portion with the fingers opening is configured to receive fingers but not a thumb of the hand during the wearing of the pillow sleeve device by the user. Therefore, the fingers of the user may be exposed and not covered by the hand portion of the main body when worn by the user.

The hand portion with the thumb opening of the main body is configured to receive only the thumb of the hand during the wearing of the pillow sleeve device by the user. Therefore, the thumb may be exposed and not covered by the hand portion of the main body when worn by the user. The thumb opening may be elongate and arranged on a thumb opening axis that is spaced apart from and oriented substantially parallel with the central axis of the main body. Advantageously, the thumb opening is configured to receive the thumb regardless of the thumb being on the hand of a right arm or a left arm of the user. In other words, the pillow sleeve device may be ambidextrous due to the location and orientation of the thumb opening of the main body.

The main body of the pillow sleeve device may also have a wrist portion disposed between the arm portion and the hand portion, in certain examples.

In another embodiment, a method for manufacturing a pillow sleeve device includes steps of providing at least one flexible shell material and at least one cushion fill material. The method may further include a step of measuring a forearm of a user to provide user measurements. Subsequent to the measuring step, the method may then include a step of selecting an appropriate size for the pillow sleeve device based on the user measurements. The method will then include a step of creating a sewing pattern with the user measurements. The method will then involve a step of applying the sewing pattern to at least one flexible shell material according to the sewing pattern. Next, the applying step can be performed by either folding or cutting the at least one flexible shell material, in order to provide at least one flexible shell with two layers of the at least one flexible shell material. The method may then include a step of sewing the at least one flexible shell to provide an enveloping volume for filling with the at least one cushion fill material. Subsequently, the method also includes a step of filling the enveloping volume of the at least one flexible shell with the at least one cushion fill material to provide at least one cushion fill. In order to complete the manufacturing method, a step involving sewing ends of the at least one flexible shell to construct the pillow sleeve device is then performed.

In a further embodiment, a method for resting or sleeping includes a step of providing the pillow sleeve device as described. Next, the method may include a step of selecting, by the user, either the right arm or the left arm on which to wear the pillow sleeve device. The method then includes a step of inserting, by the user, the hand and the arm of the user through the arm opening of the main body. Next, the method involves a step of disposing, by the user, the fingers of the hand through the fingers opening of the main body. The method then involves a step of placing, by the user, the thumb of the hand through the thumb opening of the main body. Subsequently, the method involves a step of resting, by the user, a head of the user on either the arm portion or the hand portion of the main body. The user may thereby be permitted to rest or sleep on the soft resting surface of the main body regardless of the location.

In a particular embodiment, a pillow sleeve that is portable and provides means for the user to sleep anywhere is provided. The pillow sleeve is durable, lightweight, machine washable, and can be used on either arm. The pillow sleeve can be designed with multiple variations such as cartoon characters, sports teams, animals, and more. The pillow sleeve can be tubular and elongated. The pillow sleeve can come in different sizes and may further come in a short sleeve which sits below the elbow or a long sleeve version which can cover the elbow. The pillow sleeve can be made of a soft material and may include a puffed up sleeve which adds extra padding and cushioning to the head of the user when sleeping against the pillow sleeve. The pillow sleeve may be provided with a large opening for the user to slip the arm of the user through. The pillow sleeve may further be provided with at least two additional openings disposed opposite the large opening, so that the user can slip the hand of the user therethrough with the fingers of the user extending through one of the additional openings and the thumb of the user extending through another of the additional openings.

In exemplary embodiments, the pillow sleeve device, system, and method of the present disclosure solves a common problem of a user of being uncomfortable while sleeping on an arm of the user wherever they are located. The present disclosure provides for a more comfortable sleeping option for wherever the user decides to lay their head. Another problem with known pillow sleeve devices is that they do not cover the whole forearm, and also the user cannot dispose known pillow sleeve devices all the way over the arm like the user would with a sleeve of a shirt. The present disclosure improves on these other known pillow sleeve devices by being very lightweight, portable, usable on both arms of the user, and by actually covering the entire forearm instead of the area of the arm just going under the pillow portion of the device.

In particular examples, the pillow sleeve device, system, and method of the present disclosure solves the problem of the user being uncomfortable while sleeping on their arm wherever they are located. Advantageously, the herein disclosed pillow sleeve device, system, and method gives the user a more comfortable sleeping option for wherever they decide to lay their head down to sleep.

In certain examples, the pillow sleeve device, system, and method of the present disclosure provides a pillow gauntlet, which is a variety of glove with a long cuff, which slips over the arm of the user and can be used anywhere they want to sleep. The present pillow sleeve device, system, and method also minimizes or eliminates the problem of the user being uncomfortable while lying on their arm.

In additional examples, the pillow sleeve device, system, and method actually goes over or covers the arm of the user. The pillow sleeve device, system, and method of the present disclosure may also have a thumbhole through which the thumb of the user may be disposed while in use. Beneficially, the location and orientation of the thumbhole on the pillow sleeve device, system, and method allows for it to be used for both arms instead of just one of the arms of the user. In other words, the pillow sleeve device, system, and method of the present disclosure is not necessarily provided in left- and right-handed versions, but instead may be provided as a single device usable for either the left or right side arms of the user, as desired.

In yet further examples, the pillow sleeve device, system, and method of the present disclosure can be placed on either arm, which differs from conventional pillow sleeves known in the art that do not work well because the user has to keep their arm in a fixed position in order for them to sleep comfortably. The configuration of the pillow sleeve device, system, and method of the present disclosure allows the user to sleep on any side of a bed, as desired, and to use the pillow sleeve device, system, and method anywhere because of both the portability and flexibility provided by the unique configuration of the present disclosure.

In yet other examples, the pillow sleeve device, system, and method of the present disclosure is also very lightweight, and portable, works on both arms, and actually covers the entire forearm instead of the arm just being located under the pillow.

Various additional examples of the pillow sleeve device, system, and method involves the employment of at least one of: 1) cotton; 2) faux fur; and 3) stitching. With respect to the relationship between the various components of the pillow sleeve device, system, and method, it should be appreciated that an interior of the pillow device may be stuffed with cotton, and the faux fur may be placed over the exterior to provide maximum comfort. Everything is then stitched together to finish the pillow sleeve device.

In yet more examples, the method of using the pillow sleeve device and system includes placing the pillow sleeve device over the arm of the user.

One Example of How To Make The Pillow Sleeve Device:

First of all, the user or manufacturer may take measurements from the forearm of the user to the middle of the palm on the hand of the user. Then, based on the measurements taken, an appropriate size for the pillow sleeve device may be selected by the user or manufacturer, e.g., the size could be either small, medium, or large.

Either the user or a manufacturer may then proceed to create a sewing pattern with those measurements. The sewing pattern has a predetermined shape configured for it to look like a pillow sleeve device upon being constructed.

To construct the pillow sleeve device according to this particular method, either the user or the manufacturer may use one piece of fabric without cutting it. The user or manufacturer may then put the pattern on the fabric to get the appropriate size, and then fold the fabric in itself to have two layers. The user or manufacturer may then sew both layers together and then fill it with a cushion fill such as cotton.

The user or manufacturer may then also place the pattern over again, but in this case the user or manufacturer does not fold it. After placing the pattern over to have one measure, the user or manufacturer may measure the same amount two more times (i.e., repeat the first step to have the two layers and sew them). After sewing those layers by the user or manufacturer, the user or manufacturer may fill them also with the cushion fill such as cotton.

Subsequent to these steps, the user or manufacturer will have three (3) different parts, i.e., the two (2) sides filled with the cushion fill such as cotton, and the middle with one layer. The user or manufacturer may then sew together both ends, and the pillow sleeve device is thereby completed.

It should be appreciated that the cushion fill, such as the cotton as one non limiting example, may be most important to the comfort of the user. Once can change the flexible material such as the fabric that is used, e.g., by using softer fabrics or different stitching, to also facilitate the making of the soft and comfortable surface for the user to rest or sleep on in use.

One Example of How To Use The Pillow Sleeve Device:

In operation, the user may place the pillow sleeve device over the arm of the user and then sleep on the pillow sleeve device.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1B is a block diagram extending from FIG. 1A and further illustrating the pillow sleeve device according to one embodiment of the present disclosure.

FIG. 2B is a block diagram extending from FIG. 2A and further illustrating the pillow sleeve device according to further embodiments of the present disclosure.

FIG. 3B is a block diagram extending from FIG. 3A and further illustrating the pillow sleeve device according to additional embodiments of the present disclosure.

FIG. 4B is a block diagram extending from FIG. 4A and further illustrating the pillow sleeve device, according to yet other embodiments of the present disclosure.

FIG. 6A is a block diagram further illustrating the pillow sleeve device from FIG. 1A, according to some more embodiments of the present disclosure.

FIG. 12 is a right-side elevational view of the pillow sleeve device shown in FIG. 9.

FIG. 13 is a left-side elevational view of the pillow sleeve device shown in FIG. 9.

FIG. 14 is a front elevational view of the pillow sleeve device shown in FIG. 9.

FIG. 15 is a rear elevational view of the pillow sleeve device shown in FIG. 9.

FIG. 18 is a top plan view of the pillow sleeve device shown in FIG. 17.

FIG. 19 is a bottom plan view of the pillow sleeve device shown in FIG. 17.

FIG. 20 is a right-side elevational view of the pillow sleeve device shown in FIG. 17.

FIG. 21 is a left-side elevational view of the pillow sleeve device shown in FIG. 17.

DETAILED DESCRIPTION

Figure 1A:
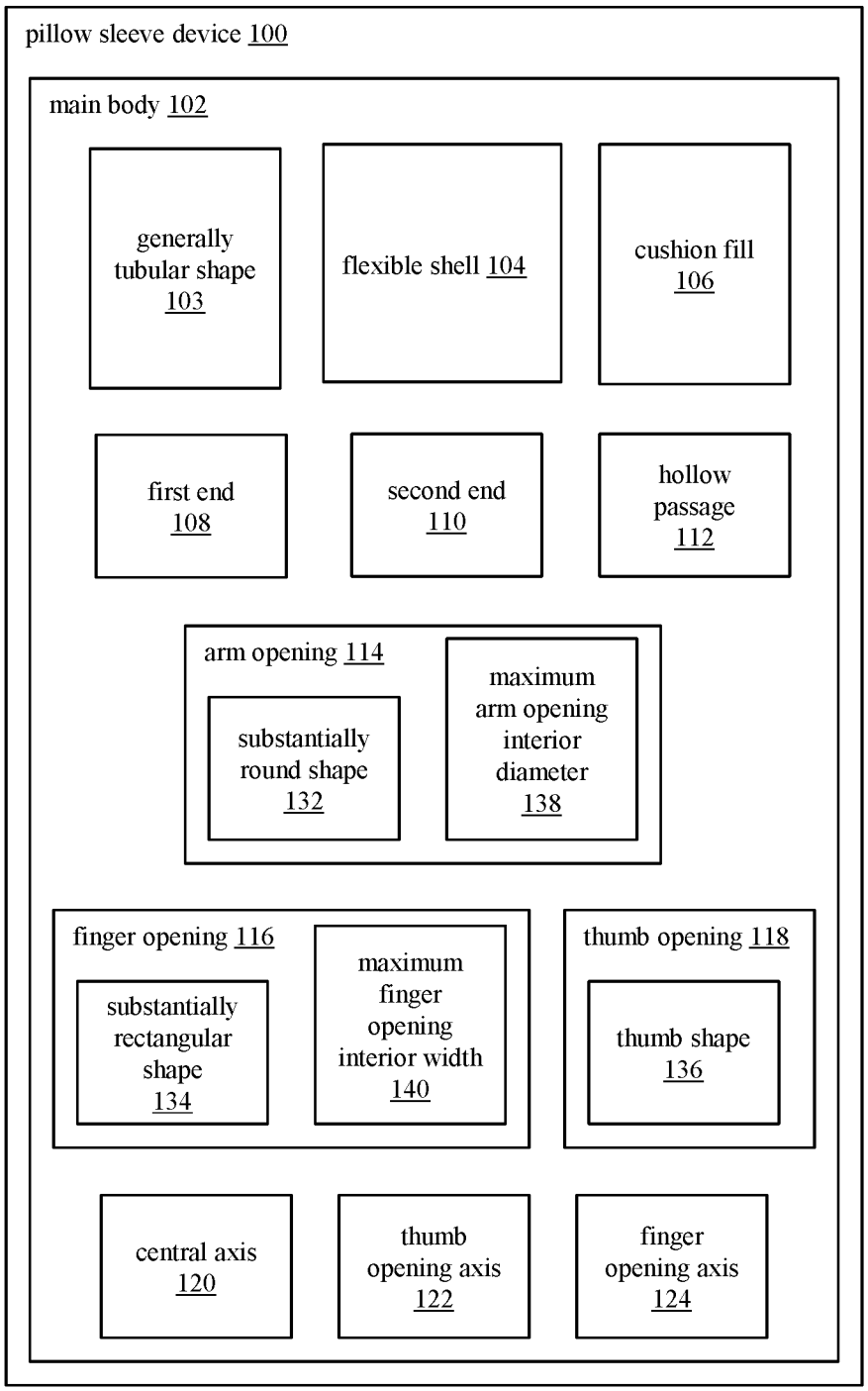
FIG. 1A is a block diagram illustrating a pillow sleeve device according to one embodiment of the present disclosure.

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. Regarding methods disclosed, the order of the steps presented is exemplary in nature, and thus, the order of the steps can be different in various embodiments, including where certain steps can be simultaneously performed, unless expressly stated otherwise. "A" and "an" as used herein indicate "at least one" of the item is present; a plurality of such items may be present, when possible. Except where otherwise expressly indicated, all numerical quantities in this description are to be understood as modified by the word "about" and all geometric and spatial descriptors are to be understood as modified by the word "substantially" in describing the broadest scope of the technology. "About" when applied to numerical values indicates that the calculation or the measurement allows some slight imprecision in the value (with some approach to exactness in the value; approximately or reasonably close to the value; nearly). If, for some reason, the imprecision provided by "about" and/or "substantially" is not otherwise understood in the art with this ordinary meaning, then "about" and/or "substantially" as used herein indicates at least variations that may arise from ordinary methods of measuring or using such parameters.

All documents, including patents, patent applications, and scientific literature cited in this detailed description are incorporated herein by reference, unless otherwise expressly indicated. Where any conflict or ambiguity may exist between a document incorporated by reference and this detailed description, the present detailed description controls.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components, or process steps, the present technology also specifically includes embodiments consisting of, or consisting essentially of, such materials, components, or process steps excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, all compositional percentages are by weight of the total composition, unless otherwise specified. Disclosures of ranges are, unless specified otherwise, inclusive of endpoints and include all distinct values and further divided ranges within the entire range. Thus, for example, a range of "from A to B" or "from about A to about B" is inclusive of A and of B. Disclosure of values and ranges of values for specific parameters (such as amounts, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, 3-9, and so on.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures.

Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The present technology improves upon pillow sleeve devices, systems, and methods known in the art.

Figure 29:
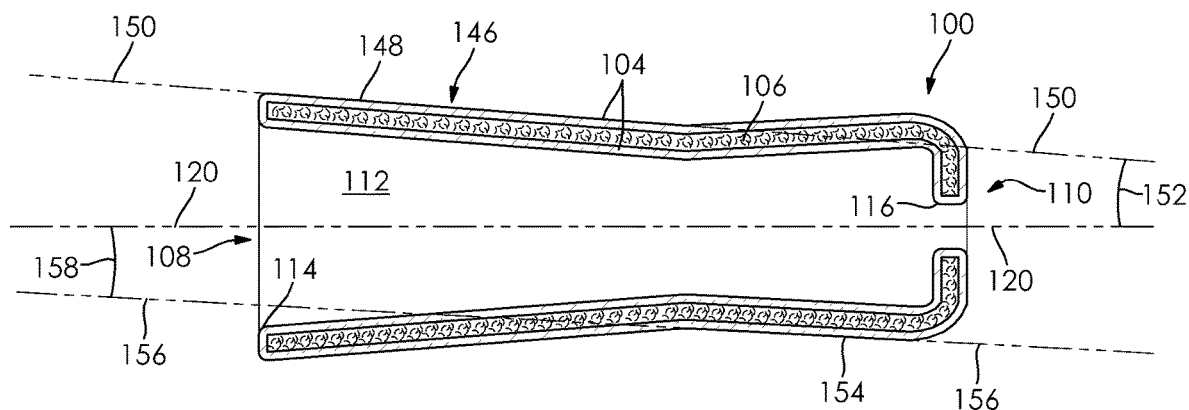
FIG. 29 is a cross-sectional front elevational view of the pillow sleeve device taken at section line A-A in FIG. 9, and further illustrating an interior of the pillow sleeve device including a flexible shell and cushion fill.
Figure 30:
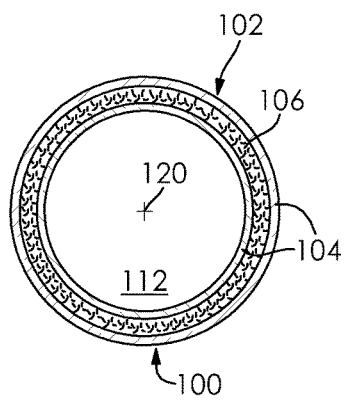
FIG. 30 is a cross-sectional side elevational view of the pillow sleeve device taken at section line B-B in FIG. 11, and further illustrating the interior of the pillow sleeve device including the flexible shell and the cushion fill.

FIGS. 1A to 1B are block diagrams that describe a pillow sleeve device 100, according to various embodiments of the present disclosure. The pillow sleeve device 100 may have a main body 102 with at least one flexible shell 104 and at least one cushion fill 106, for example, as illustrated in FIGS. 29-30. The at least one flexible shell 104 and the at least one cushion fill 106 together provide a soft resting surface for sleeping or resting by a user, in operation, and as described further herein below.

The at least one flexible shell 104 can be any suitable fabric material that is soft, durable, washable, optionally stretchable, and easy to maintain. As non-limiting embodiments, the materials forming the at least one flexible shell 104 can include woven or nonwoven polyester, cotton, blends of polyester and cotton, and the like. The at least one cushion fill can be most any soft, compressible material such as cotton, wool, or commercially available non-allergenic synthetic fiber materials such as bonded or non-bonded batting (e.g., poly fiber/down alternative) and foam rubber (open or closed cell), as non-limiting embodiments, commonly used in bed-type pillows and the like. One of ordinary skill in the art may also select other suitable types of materials for the at least one flexible shell 104 and the at least one cushion fill 106, as desired, within the scope of the present disclosure.

As shown in FIGS. 1A to 1i, the main body 102 of the present disclosure has a generally tubular shape 103. The main body 102 has a first end 108, a second end 110, and a hollow passage 112. The main body 102 also has an arm opening 114, a fingers opening 116, and a thumb opening 118. The hollow passage 112 is disposed between the first end 108 and the second end 110. The arm opening 114 is in communication with the fingers opening 116 by the hollow passage 112 of the main body 102. The hollow passage 112 is configured to receive an arm of a user, in operation.

The pillow sleeve device 100 may further be described with respect to a central axis 120, a thumb opening axis 122, and a fingers opening axis 124, all of which are described further herein and which define the various locations and orientations of the features of the pillow sleeve device 100, as also described further herein with respect to FIGS. 9-30. For example, as shown in FIGS. 9-30, the hollow passage 112 is also elongate and arranged generally on the central axis 120 of the main body 102.

With renewed reference to FIGS. 1A to 1B, the main body 102 may further have an arm portion 126 and a hand portion 128, and in particular embodiments also a wrist portion 130 (described further hereinbelow). The arm portion 126 of the main body 102 is configured to receive and be supported by at least part of an arm of the user, in operation (shown in FIGS. 16 and 24). Similarly, the hand portion 128 of the main body 102 is configured to receive and be supported by at least part of a hand of the user, in operation (also shown in FIGS. 16 and 24).

The arm portion 126 may be disposed proximal the first end 108 of the main body 102, and the hand portion 128 may be disposed proximal the second end 110 of the main body 102. It should also be appreciated that the arm portion 126 further defines the arm opening 114, which is configured to receive the hand and the arm during a wearing of the pillow sleeve device 100 by the user. Similarly, it should be appreciated that the hand portion 128 further defines the fingers opening 116, which is configured to receive fingers but not a thumb of the hand during the wearing of the pillow sleeve device 100 by the user. In this manner, the fingers of the user are exposed and not covered by the hand portion of the main body 102, in operation.

The hand portion 128 may further define the thumb opening 118. The thumb opening 118 is configured to receive only the thumb of the hand during the wearing of the pillow sleeve device 100 by the user (shown in FIGS. 16 and 24). In this manner, the thumb is exposed and not covered by the hand portion 128 of the main body 102, in operation.

Each of the arm opening 114, the fingers opening 116, and the thumb opening 118 may further be defined by at least one of stitched and folded areas of the at least one flexible shell 104, for example. At least one of the arm opening 114, the fingers opening 116, and the thumb opening 118 may also be optionally provided with an elastic material (not shown) that is disposed around the perimeter of the arm opening 114, the fingers opening 116, or the thumb opening 118, for example, underneath the stitching or the fold of the at least one flexible shell 104, as the case may be in the embodiment. Where employed, the elastic material may minimize an undesirable movement of the main body 102 relative to the arm and the hand of the user upon being fitted on the user, for example, by providing for a snug fit on the user. It is also contemplated that each of the arm opening 114, the fingers opening 116, or the thumb opening 118 may be provided with no elastic material, which may also be more comfortable for the user in operation (not shown).

Advantageously, the thumb opening 118 of the pillow sleeve device 100 of the present disclosure is elongate and arranged on the thumb opening axis 122, for example, as shown in FIGS. 9-30. The thumb opening axis 122 may be spaced apart from the central axis 120 of the main body 102 a first predetermined distance 121, for example, as shown in FIGS. 10-11 and 18-19. The thumb opening axis 122 and the central axis 120 may be oriented substantially or roughly parallel to one another, although in embodiments with a flare (described further herein) to the hand portion 128 it should be appreciated that the thumb opening axis 122 may be spaced further apart nearer the second end 110 than the thumb opening axis 122 is spaced part nearer the first end 108 of the main body 102. The thumb opening 118 is configured to receive the thumb regardless of the thumb being on the hand of a right arm or a left arm of the user. In other words, the location and orientation of the thumb opening 118 as herein defined allows for the pillow sleeve device 100 to be ambidextrous or usable equally and easily on either hand of the user.

Most advantageously, it should be appreciated that the thumb opening axis 122 may be oriented so as to bisect the length of the main body 102, such that the thumb opening 118 is not tilted upward or downward. This likewise makes the pillow sleeve device 100 ambidextrous by merely turning the pillow sleeve device 100 to allow it to be fit on another hand of the user, and the user does not have the discomfort that might otherwise result if the thumb opening axis 122 and the thumb opening 118 associated with it were not oriented in this fashion.

As shown in FIGS. 1A-6B, and as illustrated in FIGS. 10-11 and 18-19, the arm portion 126 of the main body 102 can include a forearm portion 146. The forearm portion 146 is configured receive and be supported by only a forearm of the user, in operation (shown in FIGS. 16 and 24).

In particular embodiments, as illustrated in FIGS. 10-11 and 18-19, the forearm portion 146 has a maximum forearm portion length 147. The maximum forearm portion length 147 may be selected so as to cover substantially an entire length of the forearm of the user, in operation. The maximum forearm portion length may be selected to be between about six inches (6") and about twelve inches (12"), for example. One of ordinary skill in the art may also select other suitable dimensions for the maximum forearm portion length 147 within the scope of the present disclosure, as desired.

With reference to FIGS. 1A-6B, and as illustrated in FIG. 29, in certain embodiments at least part of the forearm portion 146 may flare outwardly toward the first end 108 of the main body 102. In particular, at least part of the forearm portion 146 may have a flared forearm surface 148. The flared forearm surface 148 may be oriented on a forearm flare axis 150. The forearm flare axis 150 may be arranged at a forearm flare angle 152 relative to the central axis 120 of the main body 102. The forearm flare angle 152 is between about fifteen degrees (15°) and about forty-five degrees (45°). A skilled artisan may also select other suitable angles for the forearm flare angle 152 within the scope of the present disclosure, as desired.

As shown in FIGS. 1A-6B, and as illustrated in FIGS. 10-11 and 18-19, the main body 102 further has the wrist portion 130. The wrist portion 130 may be disposed between the arm portion 126 and the hand portion 128 of the main body 102. The wrist portion 130 is configured to receive and be supported by at least part of a wrist of a user, in operation (shown in FIGS. 16 and 24). An elastic material (not shown) may optionally be disposed about the wrist portion 130 in some embodiments and may assist in securing the pillow sleeve device 100 to the user, in operation (shown in FIGS. 16 and 24).

With reference to 1A-6B, and as illustrated in FIGS. 10-11 and 18-19, the hand portion 128 may have a maximum hand portion exterior diameter 142 and a maximum hand portion length 144, for example, as shown in FIGS. 1B and 2B. The arm portion 126 may have a maximum arm portion exterior diameter 141. The wrist portion 130 may have a maximum wrist portion exterior diameter 145. In some embodiments, the maximum wrist portion exterior diameter 145 may be less than the maximum hand portion exterior diameter 142, in particular, so as to provide a greater cushioning at the hand of the user relative to the wrist of the user. In other embodiments, the maximum arm portion exterior diameter 141 may be substantially equal to the maximum wrist portion exterior diameter 145, so as to provide substantially a same cushioning at the arm of the user relative to the wrist of the user. In a most particular embodiment, the maximum hand portion length 144 may be between about three inches (3") and about six inches (6"). It should be appreciated that other suitable dimensions for the maximum hand portion length 144 may also be selected by one skilled in the art, within the scope of the present disclosure.

With continued reference to 1A-6B, and as illustrated in FIG. 29, at least part of the wrist portion 130 may flare outwardly toward the second end 110 of the main body 102. The at least part of the wrist portion 130 may have a flared wrist surface 154. The flared wrist surface 154 may be oriented on a wrist flare axis 156. The wrist flare axis 156 may be arranged at a wrist flare angle 158 relative to the central axis 120 of the main body 102. The wrist flare angle 158 may be between about fifteen degrees (15°) and about forty-five degrees (45°). A skilled artisan may also select other suitable angles for the wrist flare angle 158 within the scope of the present disclosure, as desired.

Figure 2A:
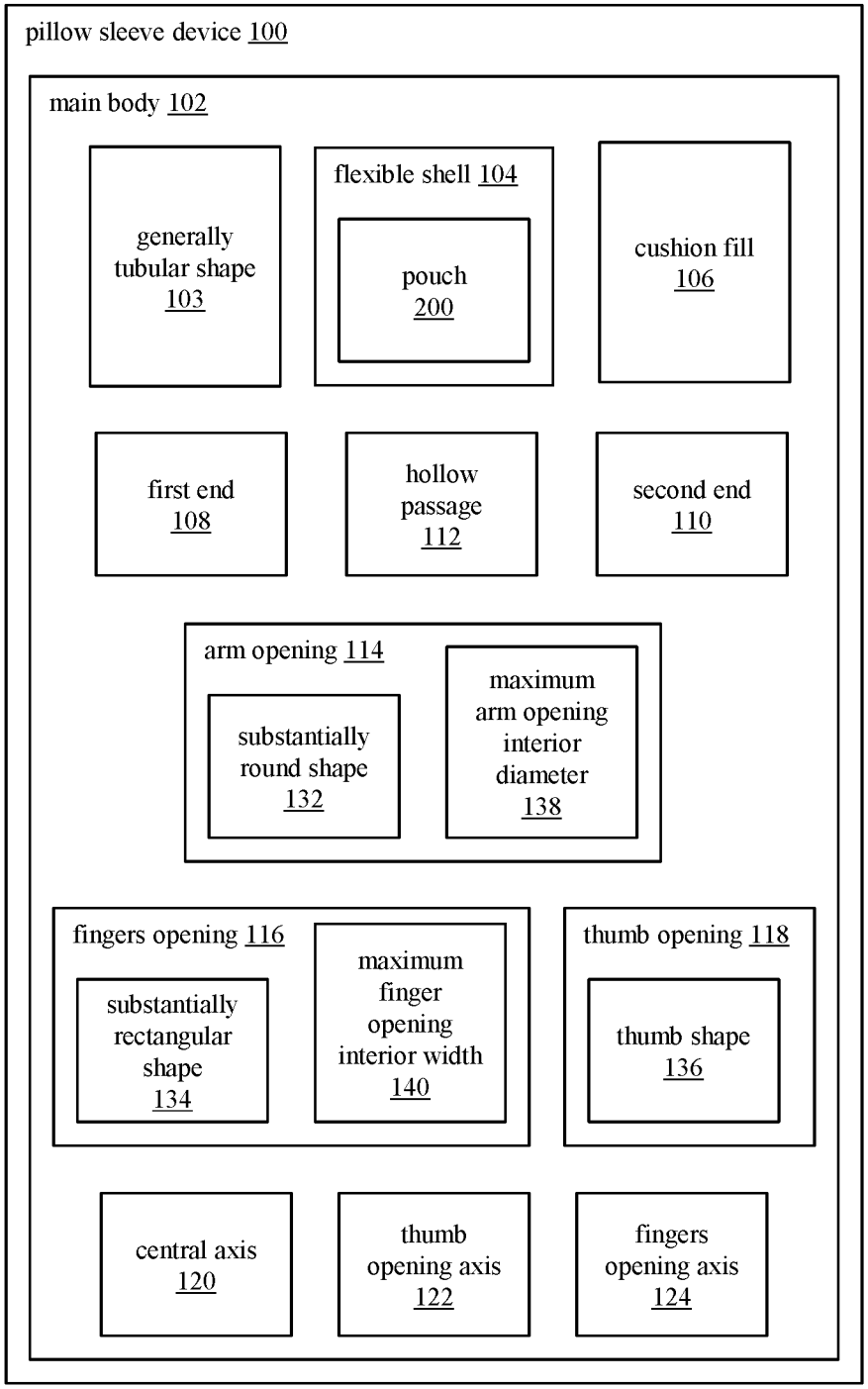
FIG. 2A is a block diagram further illustrating the pillow sleeve device from FIG. 1A, according to further embodiments of the present disclosure.

Referring now to FIGS. 2A-2B, the arm portion 126 may further include an elbow portion 202. The elbow portion 202 may be configured to be received and supported by an elbow of the user, in operation.

With additional reference to FIGS. 18-24, the forearm portion 146 may be disposed between the elbow portion 202 and the hand portion 128 of the main body 102, for example. The elbow portion 202 may be arranged on an elbow portion axis 204. For example, the elbow portion 202 may have a bend 206 formed therein, or in other examples may be flexible so as to provide the bend 206 that corresponds with an associated bending of the elbow of the user, in operation. The elbow portion axis 204 may be oriented at an elbow portion angle 208 relative to the central axis 120 of the main body 102. The elbow portion angle 208 may be between about one degree (1O) and about ninety degrees (90°). In a particular embodiment, the elbow portion angle 208 is about forty-five degrees (45°). A skilled artisan may also select other suitable angles for the elbow portion angle 208 within the scope of the present disclosure, as desired.

Referring yet again to FIGS. 1A-6B, and as illustrated in FIGS. 12-13 and 20-21, the arm opening 114 of the main body 102 may have a substantially round shape 132, the fingers opening 116 may have a substantially rectangular shape 134, and the thumb opening 118 may have a thumb shape 136. Although the fingers opening 116 is shown as being entirely open, it should be appreciated that, in some examples, partitions (not shown) appropriate to separate the individual fingers of the user when inserted through the fingers opening 116 may also be employed. The substantially round shape 132 of the arm opening 114 may be arranged substantially coaxial with the central axis 120 of the main body 102, for example. The arm opening 114 may also have a maximum arm opening interior diameter 138 that is configured to receive comfortably the arm of the user.

With reference to FIGS. 13 and 21, in particular, the maximum arm opening interior diameter 138 may be between four inches (4") and six inches (6"). Other suitable dimensions for the maximum arm opening interior diameter 138 may also be employed by one skilled in the art, within the scope of the present disclosure.

As shown yet again by FIGS. 1A-6B, and illustrated in FIGS. 12-13 and 20-21, the fingers opening 116 of the main body 102 may be elongate and arranged on a fingers opening axis 124. The fingers opening axis 124 may have a substantially rectangular shape 134, for example, as shown in FIGS. 9-30. In particular embodiments, the rectangular shape 134 may have rounded corners as well, which it should be understood provides additional comfort to the user when wearing the pillow sleeve device 100. The fingers opening axis 124 may have a maximum fingers opening interior width 140, illustrated in FIGS. 12-13 and 20-21, which will define a length of the rectangular shape 134, in certain embodiments. The fingers opening axis 124 may also be oriented at a fingers opening angle 139 relative to the thumb opening axis 122.

With continued reference to FIGS. 9-30, the fingers opening angle 139 may be between about seventy-five degrees (75°) and one hundred and five degrees (105°). In a particular embodiment, the fingers opening angle 139 may be substantially ninety degrees (90°). The maximum fingers opening interior width 140 may also be between about four inches (4") and about six inches (6"). A skilled artisan may also select other suitable angles for the fingers opening angle 139, and other suitable dimensions for the maximum fingers opening interior width 140, within the scope of the present disclosure, as desired.

Figure 22:
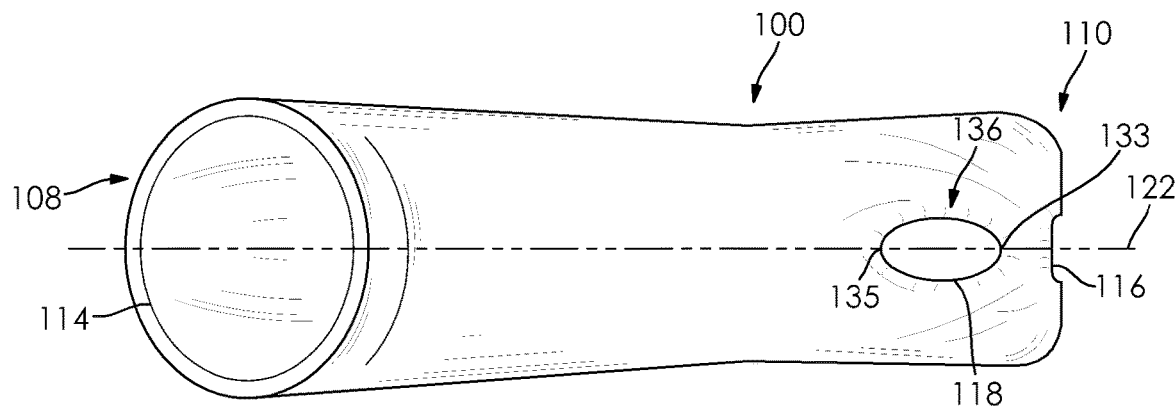
FIG. 22 is a front elevational view of the pillow sleeve device shown in FIG. 17.
Figure 23:
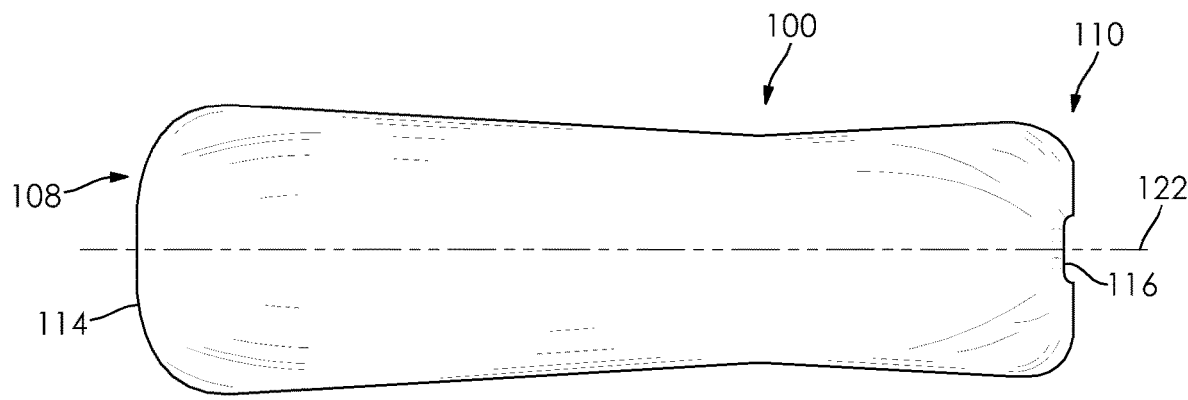
FIG. 23 is a rear elevational view of the pillow sleeve device shown in FIG. 17.
Figure 24:
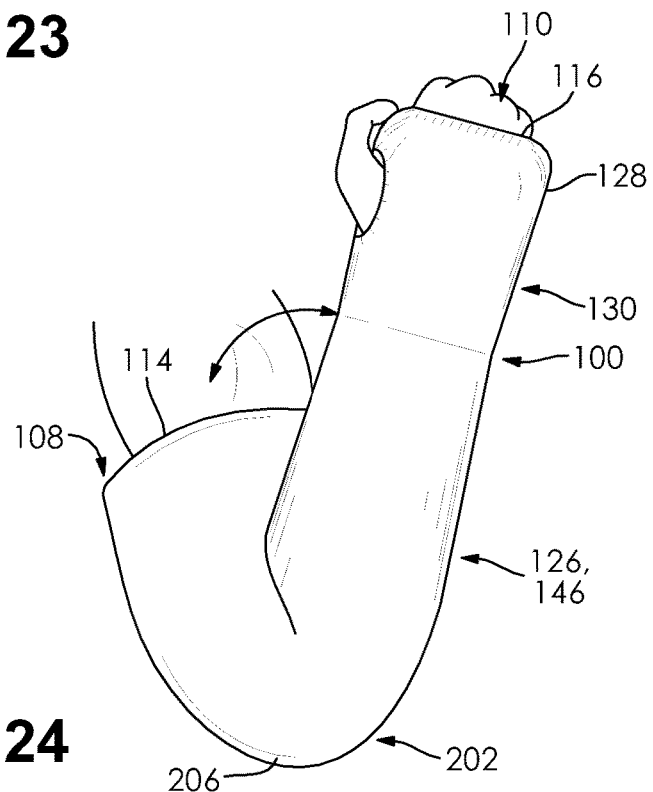
FIG. 24 is a top perspective view of the pillow sleeve device shown in FIG. 17, illustrated in use on the forearm, the hand, and the elbow of the user.

Further referring to 1A-6B, and as illustrated in FIGS. 14 and 22, the thumb opening 118 may include a predetermined thumb shape 136 that is configured to be comfortably worn by the user. The predetermined thumb shape 136 may be one of an ovoid shape (shown) and a teardrop shape (not shown), as non-limiting embodiments. The predetermined thumb shape 136 may have a rounded forward section 133 that is proximal to the fingers opening 116. Where the predetermined thumb shape 136 is the ovoid shape, the predetermined thumb shape 136 may also have a rounded rear section 135 that is distal from the fingers opening 116. Where the predetermined thumb shape 136 is the teardrop shape, the predetermined thumb shape 136 may have an angular rear section 135 that is distal from the fingers opening 116. Other suitable shapes for the predetermined thumb shape 136 of the thumb opening 118 may also be used within the scope of the present disclosure.

Figure 28:
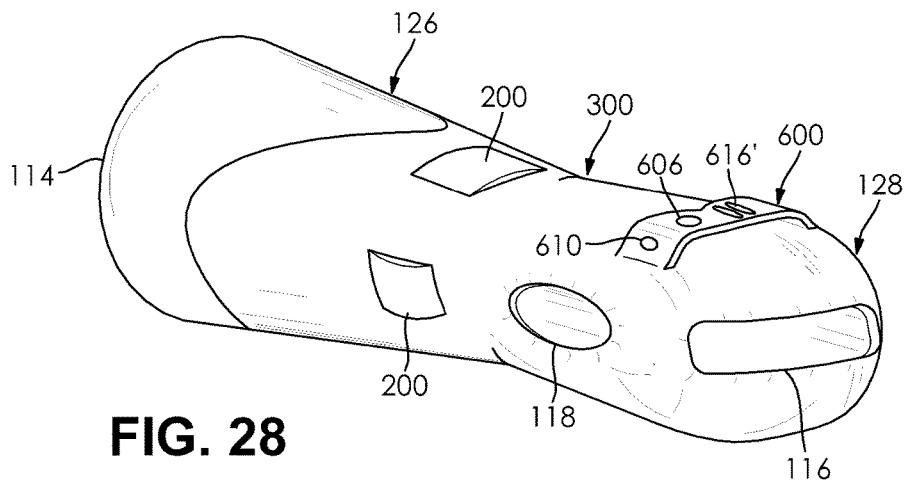
FIG. 28 is a top perspective view of a pillow sleeve device according to yet a further embodiment of the disclosure, shown with a control panel disposed on the main body of the pillow sleeve device.

Referring again to FIGS. 2A to 2B, and as illustrated in FIG. 28, the at least one flexible shell 104 may further have at least one pouch 200. The at least one pouch 200 may be configured for receiving items to be held by the user. In a particular embodiment, the at least one pouch 200 may be disposed on one of the arm portion 126, the wrist portion 130, and the hand portion 128. The at least one pouch 200 may also be selectively secured closed with one or more pouch fasteners (not shown), such as a hook-and-loop fastener, as a non-limiting embodiment. One of ordinary skill in the field may also select other suitable locations for the at least one pouch 200, as well as other suitable pouch fasteners, as desired.

Figure 3A:
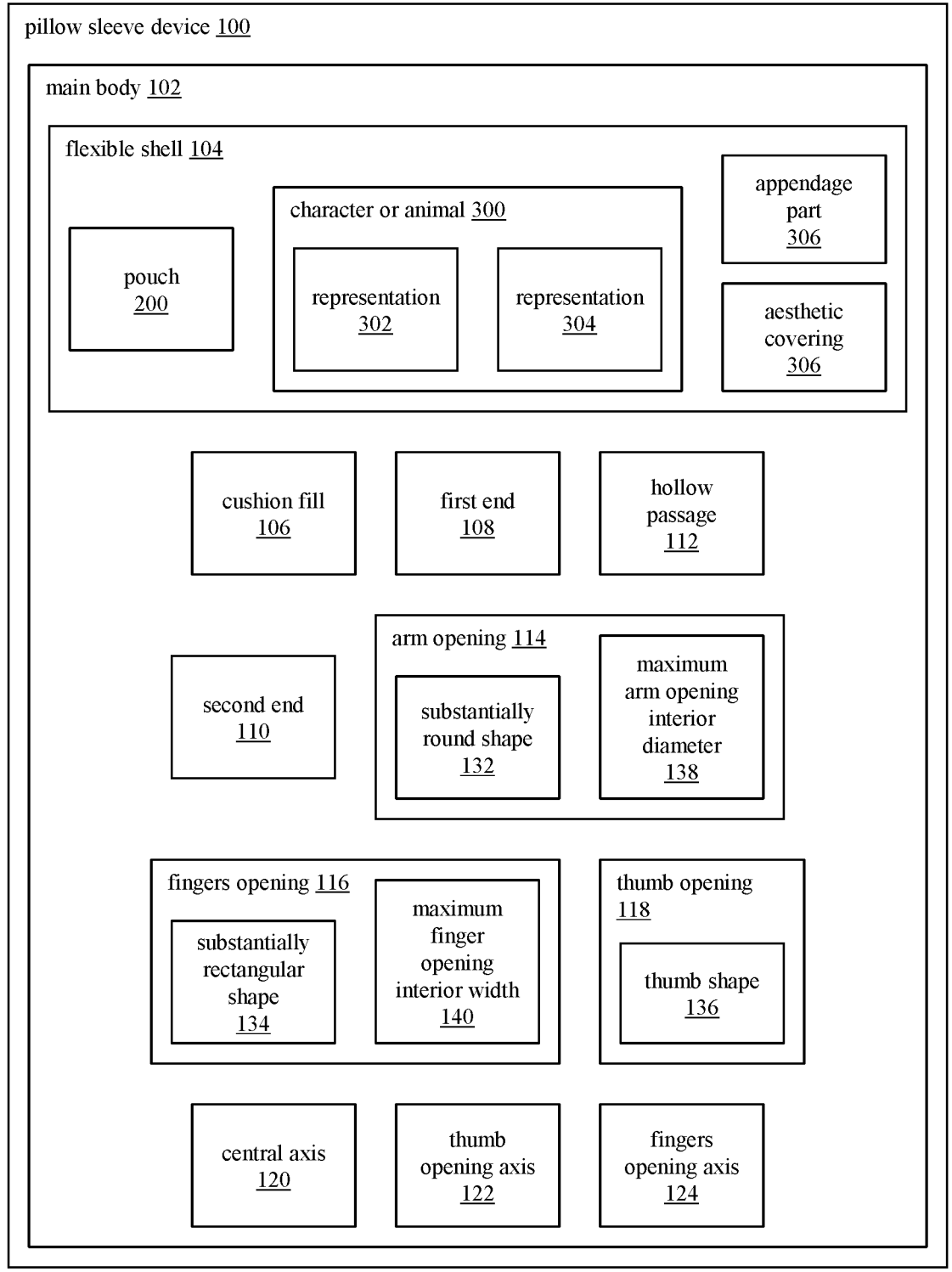
FIG. 3A is a block diagram further illustrating the pillow sleeve device from FIG. 1A, according to additional embodiments of the present disclosure.
Figure 25:
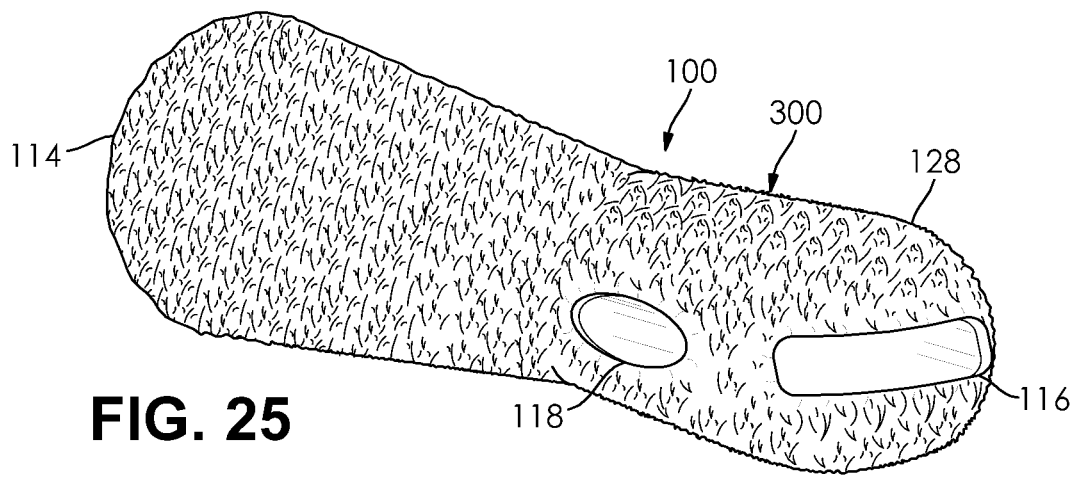
FIG. 25 is a top perspective view of a pillow sleeve device according to another embodiment of the disclosure, shown with a faux fur cover.
Figure 27:
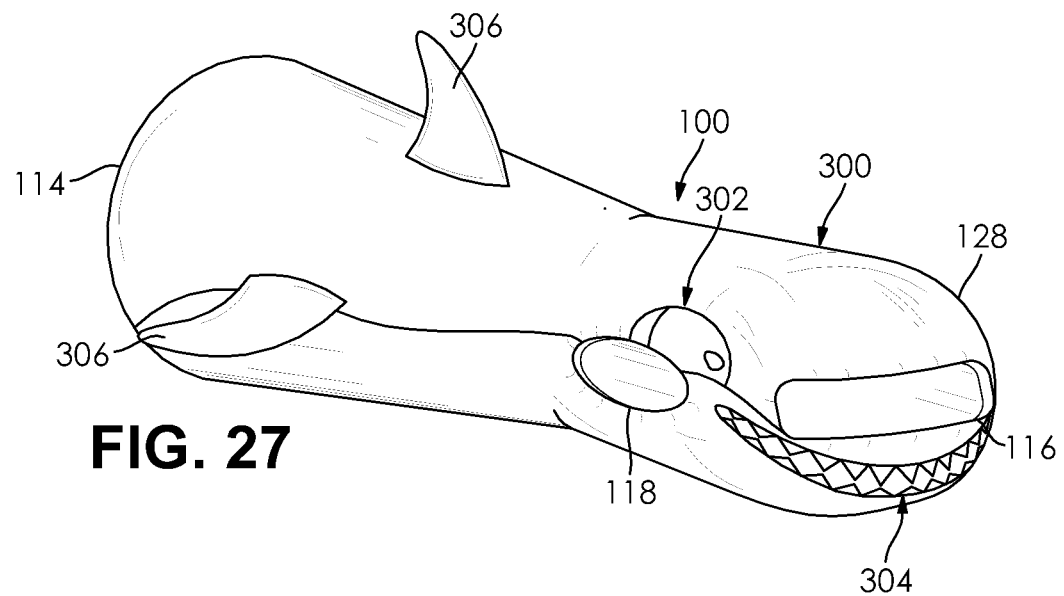
FIG. 27 is a top perspective view of a pillow sleeve device according to a further embodiment of the disclosure, shown with a character or animal representation, namely, a shark face and fins, on a main body of the pillow sleeve device.

In particular embodiments, as shown in FIGS. 3A to 3B, and as illustrated in FIGS. 25 and 27, the at least one flexible shell 104 may have a character or animal representation 300 disposed on the at least one flexible shell 104. For example, the character or animal representation 300 may be disposed on the hand portion 128 of the main body 102. As illustrated in FIG. 27, for example, the character or animal representation 300 may include a first representation 302 of an eye. The first representation 302 may be disposed adjacent to the thumb opening 118, for example. Similarly, the character or animal representation 300 may include a second representation 304 of a mouth. The second representation may be disposed adjacent to the fingers opening 116, for example.

In further embodiments, as illustrated in FIG. 27, the at least one flexible shell 104 may also have at least one appendage part 306 attached to the at least one flexible shell 104, for example. The at least one appendage part 306 may be attached either permanently or removably to the at least one flexible shell 104. The at least one appendage part may be provided in a shape of a body part of the character or animal representation 300, for example, such as an arm, a hand, a leg, a foot, a wing, a tail, or a fin.

In yet additional embodiments, as illustrated in FIG. 25, the at least one flexible shell 104 may also have an aesthetic covering 308, for example, a faux fur covering as shown, or another type of covering such as a faux scales covering or faux feathers covering, associated with the character or animal representation 300. Other suitable types, locations, appendage parts, and coverings associated with the character or animal representations 300 on the at least one flexible shell 104 of the main body 102 may also be employed, as desired.

Figure 4A:
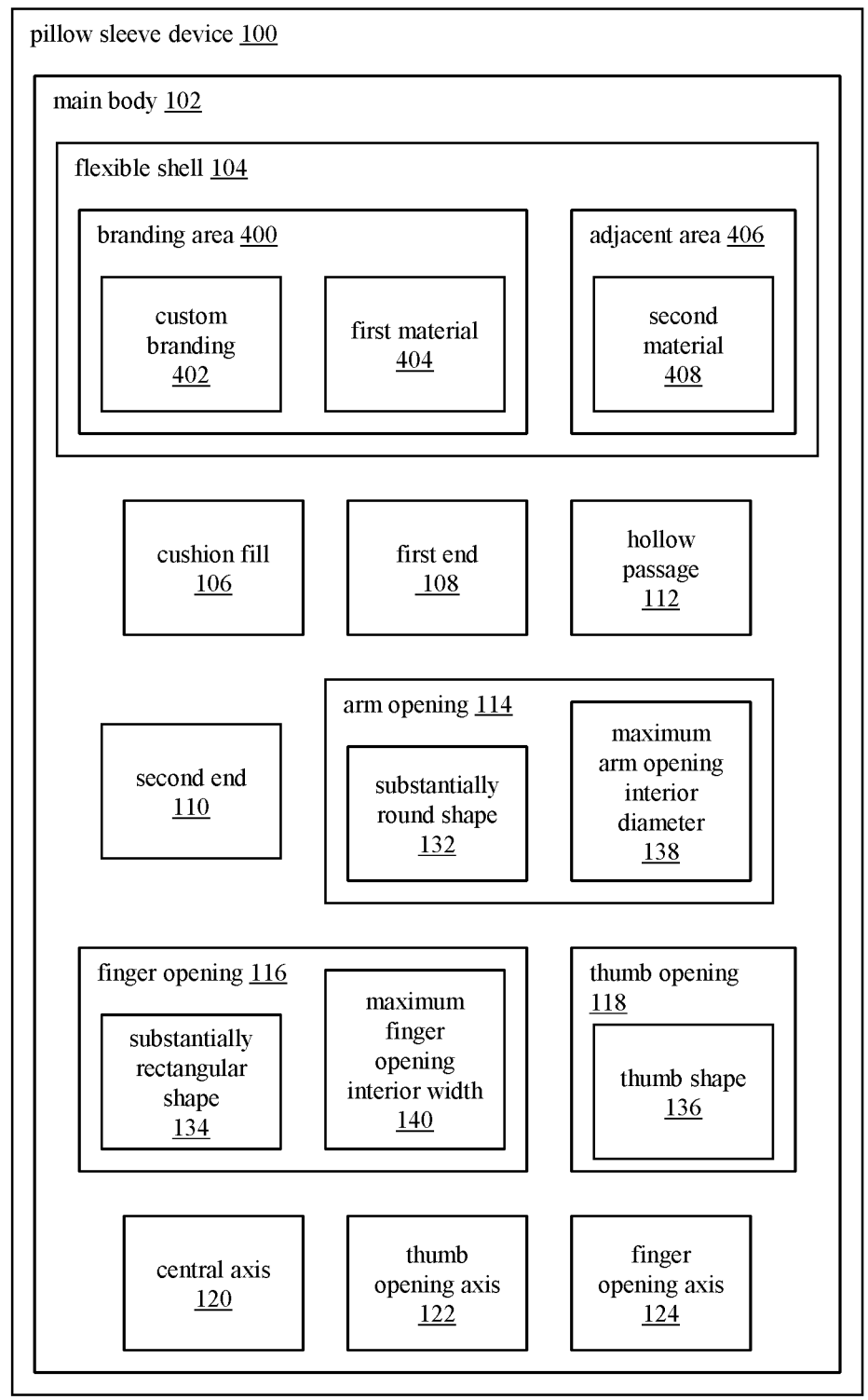
FIG. 4A is a block diagram further illustrating the pillow sleeve device from FIG. 1A, according to yet other embodiments of the present disclosure.
Figure 26:
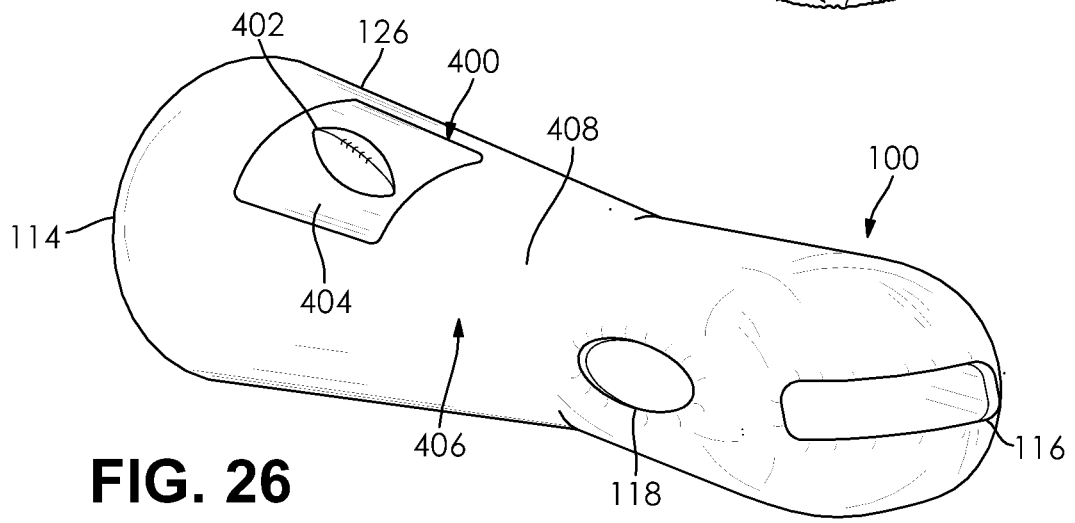
FIG. 26 is a top perspective view of a pillow sleeve device according to yet another embodiment of the disclosure, shown with a branding on a branding area of the pillow sleeve device.

With reference to FIGS. 4A to 4B, and as illustrated in FIG. 26, it should be appreciated that the at least one flexible shell 104 may have a branding area 400. The branding area 400 may be configured to receive a custom branding 402, such as a logo or graphic, as non-limiting embodiments. In a particular embodiment, the branding area 400 may be located on the arm portion 126 of the main body 102. The branding area 400 of the at least one flexible shell 104 may also include a first material 404. An adjacent area 406 to the branding area 400 may also include a second material 408. It should be appreciated that the first material 404 may be different from the second material 408, with the second material 408 being disposed in an adjacent area 406 of the at least one flexible shell 104 relative to the first material 404.

Advantageously, in particular embodiments the first material 404 may be configured to receive the custom branding 402 and the second material 408 may not be configured to receive the custom branding 402. In this manner, the second material 408 may be selected for comfort of the user as opposed to the first material 404 that may be selected for the ability to durably accept the custom branding 402, for example, where the custom branding 402 is printed with an ink on the branding area 400 of the at least one flexible shell 104. As non-limiting embodiments, the first material 404 may include a polyester material, and the second material 408 may include a cotton material, with the custom branding 402 being printed with a wash durable ink onto only the first material 404. One of ordinary skill in the art may also select other suitable materials, locations, and means for forming the custom branding 402 on the branding area 400 of the at least one flexible shell 104 within the scope of the present disclosure.

Figure 5A:
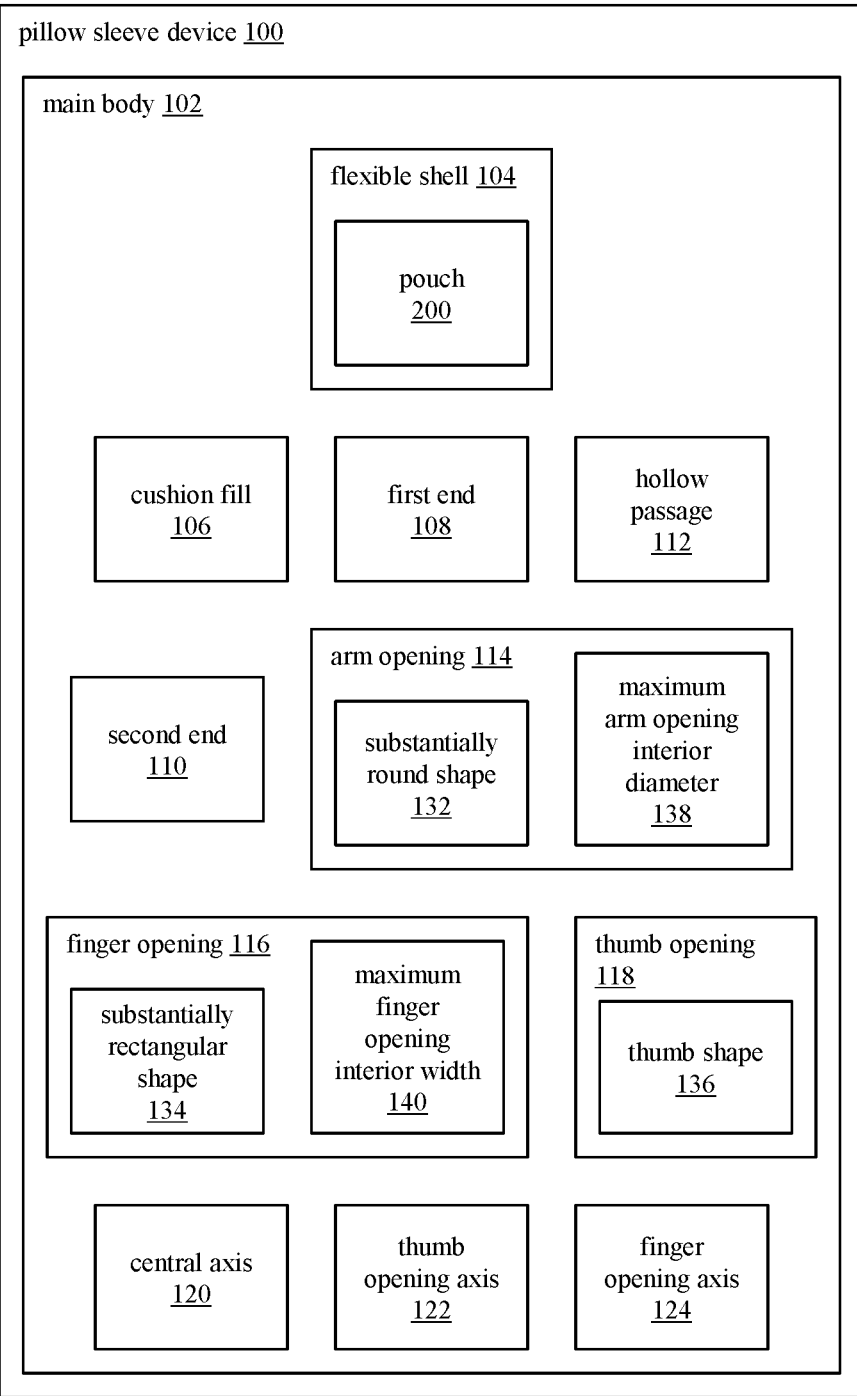
FIG. 5A is a block diagram further illustrating the pillow sleeve device from FIG. 1A, according to yet additional embodiments of the present disclosure.
Figure 5B:
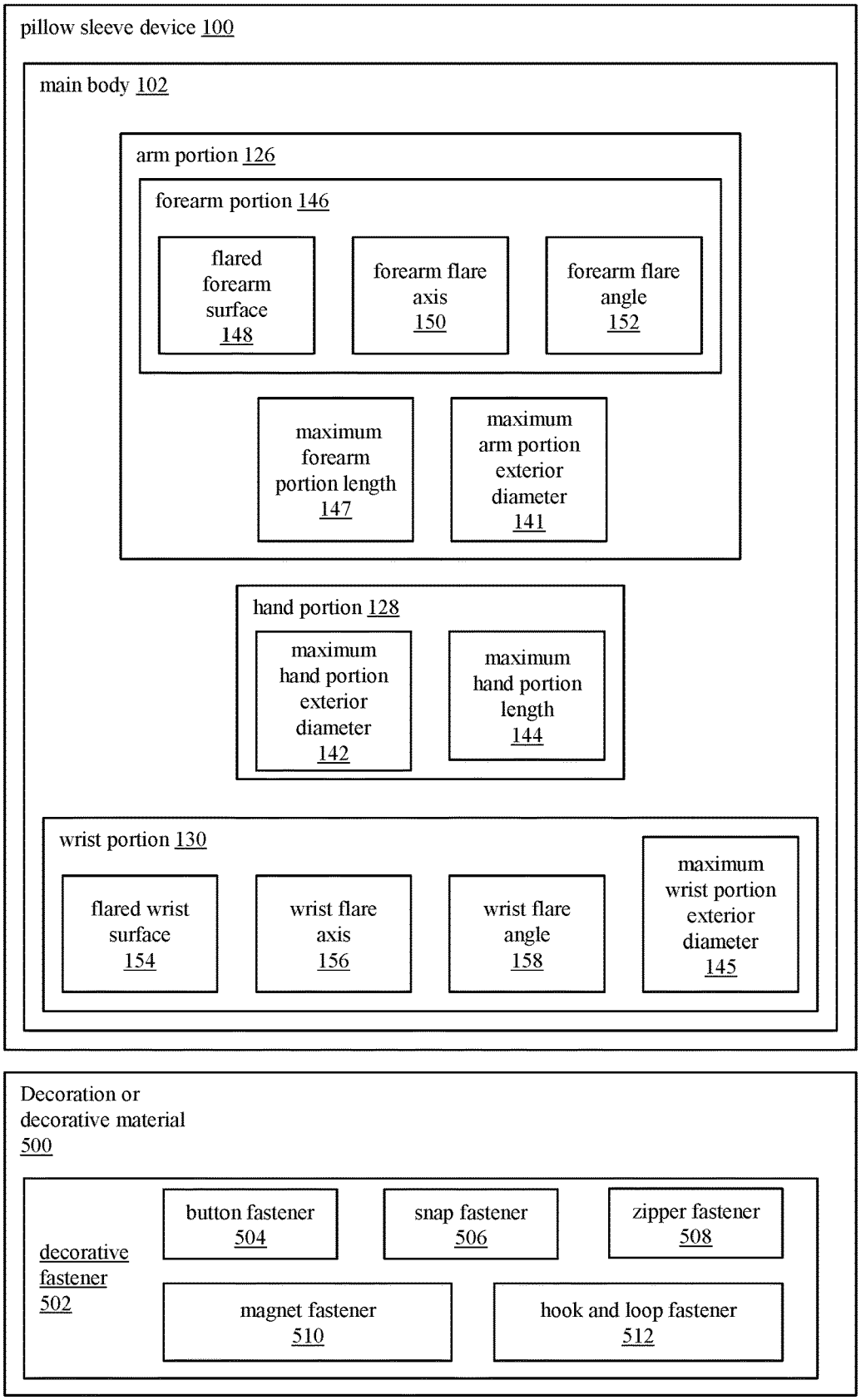
FIG. 5B is a block diagram extending from FIG. 5A and further illustrating the pillow sleeve device, according to yet additional embodiments of the present disclosure.

With reference to FIGS. 5A to 5B, the at least one flexible shell 104 may also be customizable. For example, the at least one flexible shell 104 may be customized with at least one decoration or decorative material 500. The at least one decoration or decorative material 500 may be either permanently attached or removably attached to the at least one flexible shell 104. Where the at least one decoration or decorative material 500 is removably attached to the at least one flexible shell 104, the attachment may be performed with at least one decoration fastener 502. As non-limiting embodiment, the at least one decoration fastener 502 may include one of a button fastener 504, a snap fastener 506, a zipper fastener 508, a magnet fastener 510, and a hook-and-loop-fastener 512. A skilled artisan may also select other suitable decoration fasteners 502 within the scope of the present disclosure.

Figure 6B:
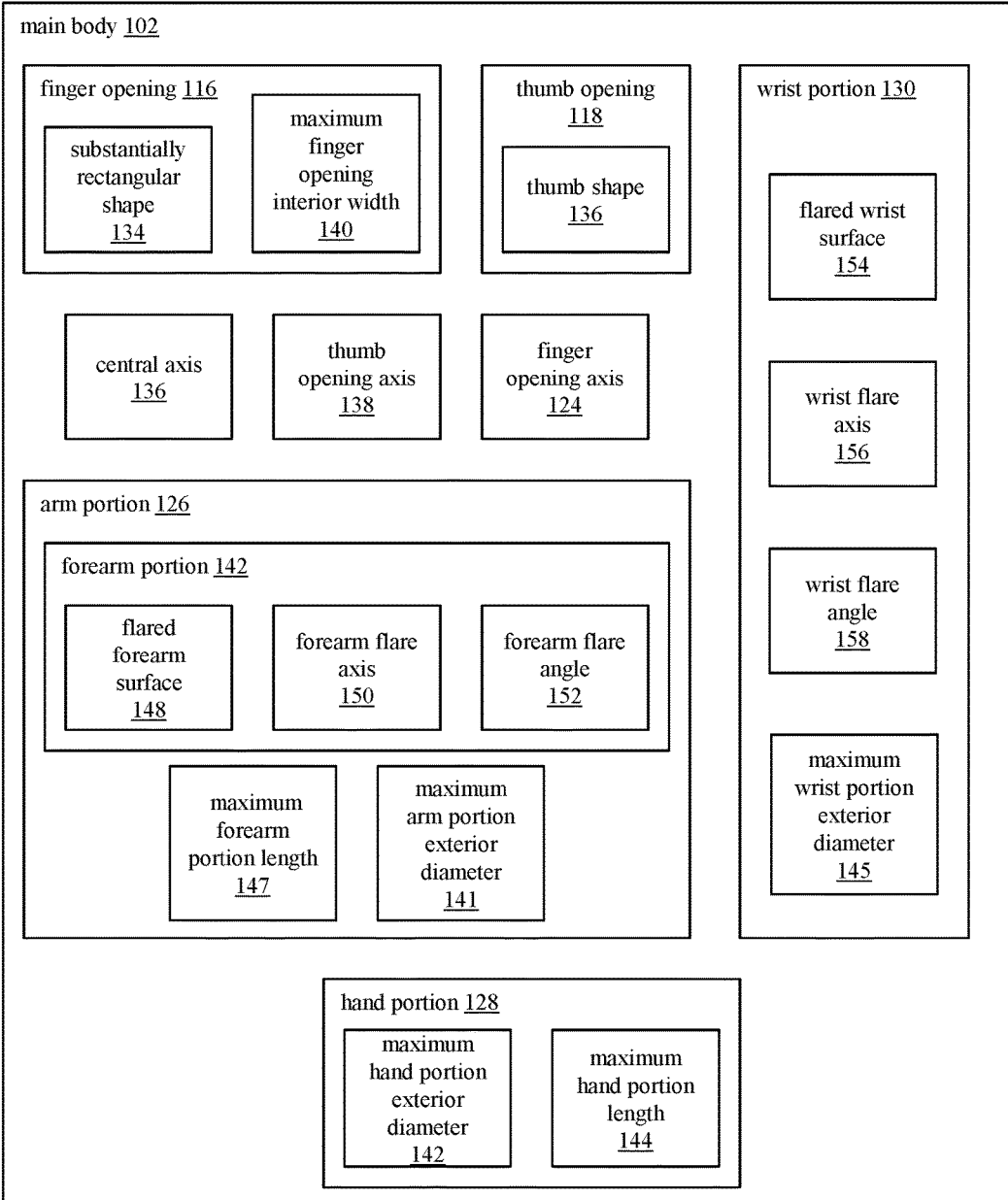
FIG. 6B is a block diagram extending from FIG. 6A and further illustrating the pillow sleeve device according to some more embodiments of the present disclosure.

Referring now to FIGS. 6A to 6B, and as illustrated in FIG. 28, in certain embodiment the at least one flexible shell 104 further envelopes an electronics package 600. The electronics package 600 may include a power source 602, a controller 604, and at least one of a visual unit 606, an auditory unit 610, and a vibratory unit 614. The at least one of the visual unit 606, the auditory unit 610, and the vibratory unit 614 may be in communication with the power source 602 and the controller 604. As non-limiting embodiments, the power source 602 may include a battery, and the controller 604 can include a microprocessor-based controller with a programmable memory used to store tangible and non-transitory program instructions and various functions thereon. The battery may be replaceable or rechargeable. A skilled artisan may also select other suitable types of the power source 602 and the controller 604, as desired.

In particular embodiments, the at least one of the visual unit 606, the auditory unit 610, and the vibratory unit 614 are configured to activate at a predetermined time by the controller 604. In this manner, it should be appreciated that the at least one of the visual unit 606, the auditory unit 610, and the vibratory unit 614 may advantageously operate as an alarm for the user when resting or sleeping.

In non-limiting embodiments, the visual unit 606 may include at least one light 608, such as an LED light, and the auditory unit 610 may include at least one speaker 612, such as a piezoelectric speaker. The at least one light 608 and the at least one speaker 612 may be disposed on the hand portion 128 of the main body 102, for example, as shown in FIG. 20. One skilled in the art may also select other suitable types and locations for the visual unit 606 and the auditory unit 610 within the scope of the present disclosure.

In yet other embodiments, the electronics package 600 may further includes a user interface 616. The user interface 616 may be in communication with the controller 604. The user interface 616 may be configured to permit the user to control e at least one of the visual unit 606, the auditory unit 610, and the vibratory unit 614. In one non-limiting embodiment, the user interface 616 is a touch screen. The user interface 616 may be arranged on the hand portion 128 of the main body 102 adjacent to but spaced part from the fingers opening 116 of the main body 102. It should be appreciated that a skilled artisan may also select other suitable locations for the user interface 616, for example, to take into account the likely location or locations that the user may wish to rest or sleep upon, in operation.

In yet further embodiments, the electronics package 600 may also include a transceiver 618. The transceiver 618 may be in communication with the controller 604, where the communication may include wireless transmission and reception such as by BLUETOOTH® or WI-FI® over either a wide area network (WAN) or a local area network (LAN). The transceiver may advantageously permit for a remote control of the electronics package 600, for example, by an other electronic device 620 of the user. In certain embodiments, the other electronic device 620 of the user is one of a computer, a mobile telephone, and a tablet with wireless internet access. The pillow sleeve device 100 may thereby be provided as part of a networked system, in other examples. One of ordinary skill in the field may also select other suitable types of both the transceiver 618 and the other electronic device 620 of the pillow sleeve device 100, as desired.

It is further contemplated that one skilled in the art may also use other types of additional electronic components and electronic devices, such as mobile devices and wearable electronic devices, with the system including the pillow sleeve device 100, within the scope of the present disclosure.

FIGS. 3A to 3B are block diagrams that further describe the pillow sleeve device 100 from FIG. 1A, according to some embodiments of the present disclosure. In some embodiments, the at least one flexible shell 104 may include at least one appendage part 306 attached to the at least one flexible shell 104. The at least one flexible shell 104 may also include a representation 300 of a character or animal disposed on the hand portion 128, and the representation 300 of the character or animal. The character or animal representation 300 may include a first representation 302, for example, of an eye disposed adjacent to the thumb-opening and a second representation 304, for example, of a mouth disposed adjacent to the fingers opening. The at least one appendage part 306 may be in a shape of a body part of a character or animal representation, for example, a fin of a shark. On skilled the art may also select other suitable images and shapes for the first representation 302, the second representation 304, and the shape of the appendage part 306, as desired.

Figure 7:
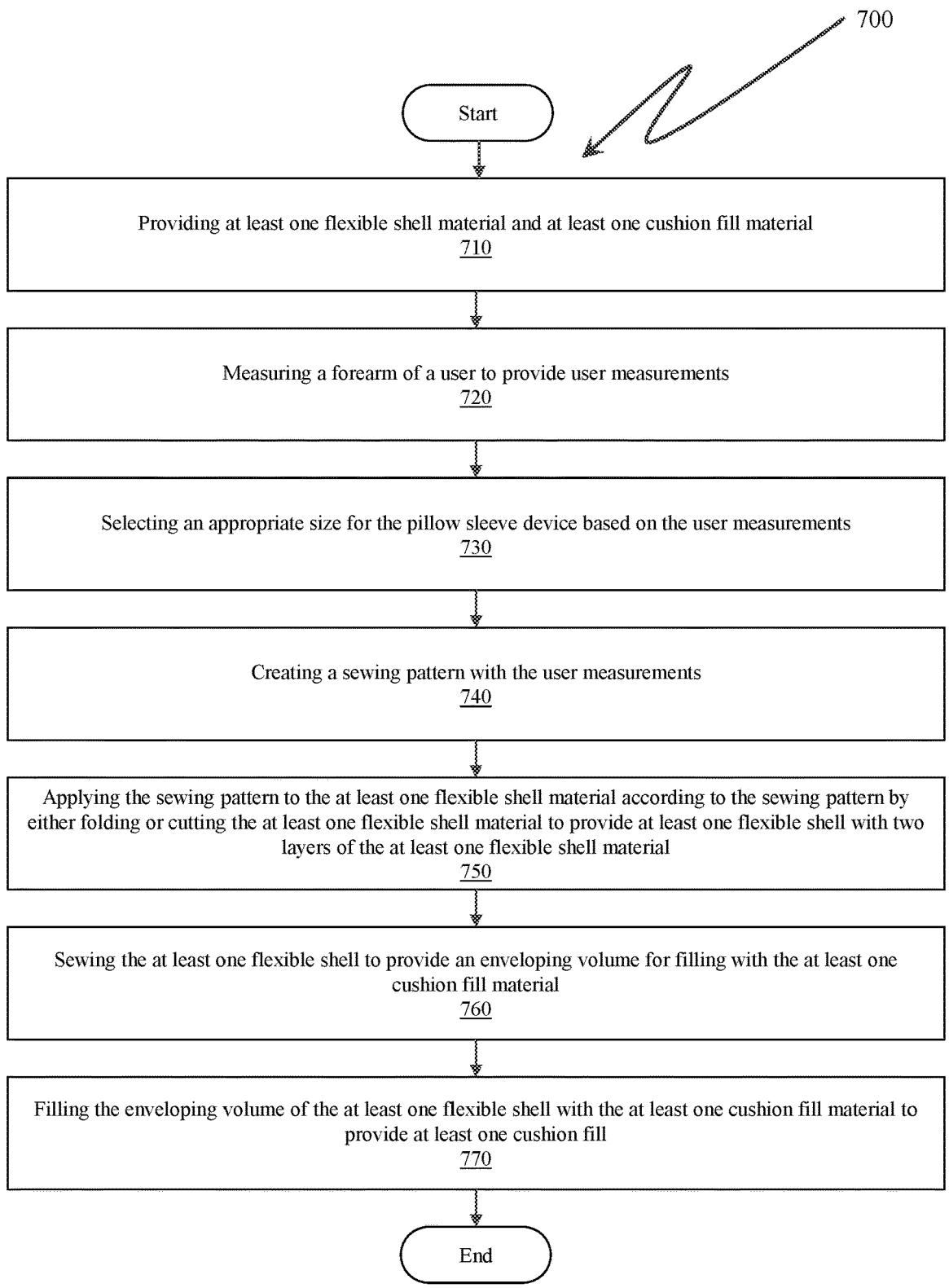
FIG. 7 is a flowchart illustrating a method for manufacturing a pillow sleeve device, according to one embodiment of the present disclosure.

It should be appreciated that the present disclosure further includes a manufacturing method 700 for manufacturing the pillow sleeve device 100, for example, as shown in FIG. 7. At step 710, the manufacturing method 700 may include providing at least one flexible shell material and at least one cushion fill material. At step 720, the manufacturing method 700 may include measuring a forearm of a user to provide user measurements. At step 730, the manufacturing method 700 may include selecting an appropriate size for the pillow sleeve device based on the user measurements. At step 740, the manufacturing method 700 may include creating a sewing pattern with the user measurements. In particular, the sewing pattern is a custom sewing pattern specific to the user measurements provided by the user.

As a non-limiting example, the step 720 may involve an inputting of the forearm measurements, made manually by the user, into an online portal or website available via the internet or a mobile application. The forearm measurements provided thusly may then be saved to a database, for example, on a server accessible to a manufacturer, which likewise may use the measurements to customize the pillow sleeve device 100 for the user during the manufacturing method 700.

In some embodiments, at step 750, the method 700 may include applying the sewing pattern to the at least one flexible shell material according to the sewing pattern by either folding or cutting the at least one flexible shell material to provide at least one flexible shell with two layers of the at least one flexible shell material. At step 760, the manufacturing method 700 may include sewing the at least one flexible shell to provide an enveloping volume for filling with the at least one cushion fill material. At step 770, the manufacturing method 700 may include filling the enveloping volume of the at least one flexible shell with the at least one cushion fill material to provide at least one cushion fill. Following steps 710 to 770, the manufacturing method 700 may further include sewing ends of the at least one flexible shell to construct the pillow sleeve device. The pillow sleeve device 100 may thereby be provided.

Figure 8:
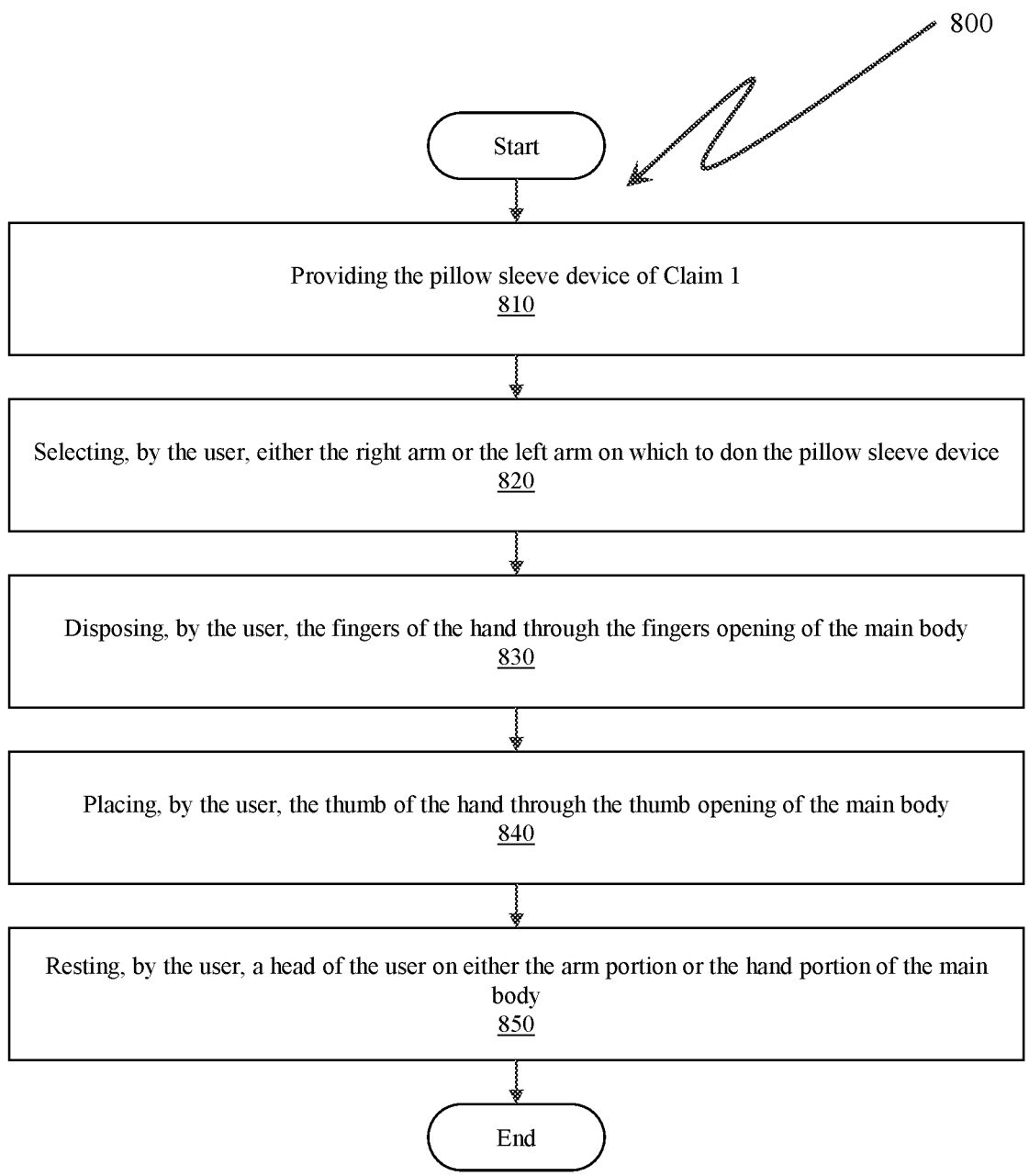
FIG. 8 is a flowchart illustrating a method for resting or sleeping by using a pillow sleeve device, according to one embodiment of the present disclosure.
Figure 9:
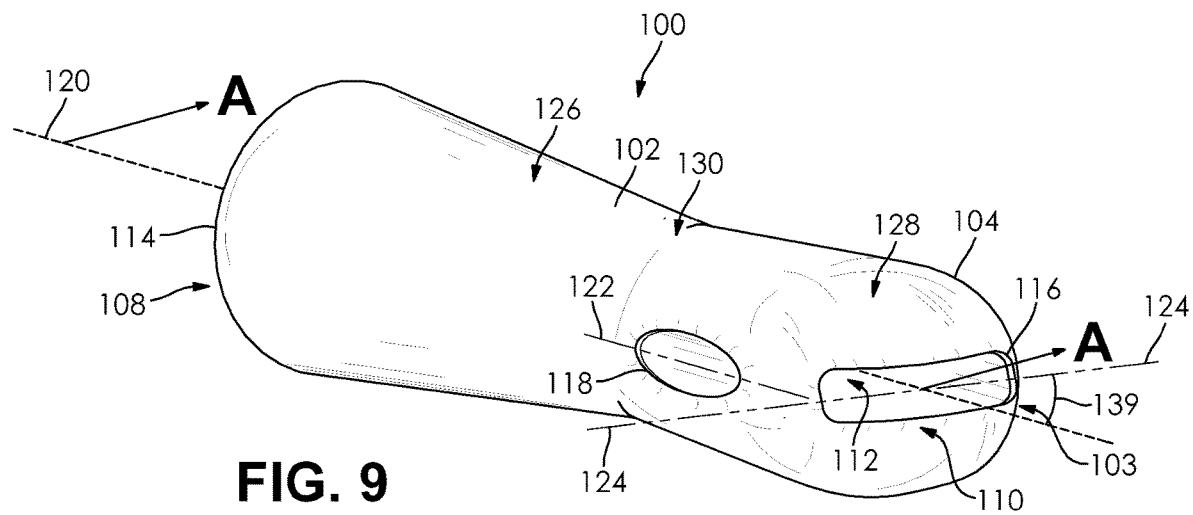
FIG. 9 is a top perspective view of a pillow sleeve device according to one embodiment of the present disclosure, the pillow sleeve device configured for placement on only the forearm and the hand of a user.
Figure 10:
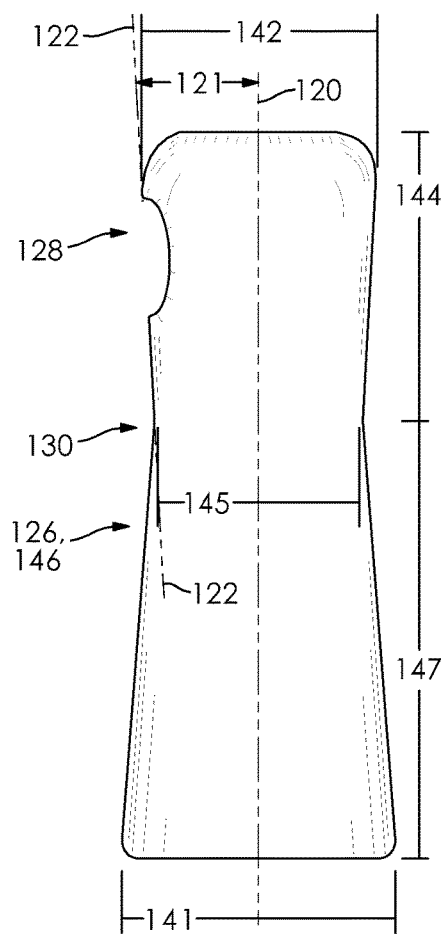
FIG. 10 is a top plan view of the pillow sleeve device shown in FIG. 9.
Figure 11:
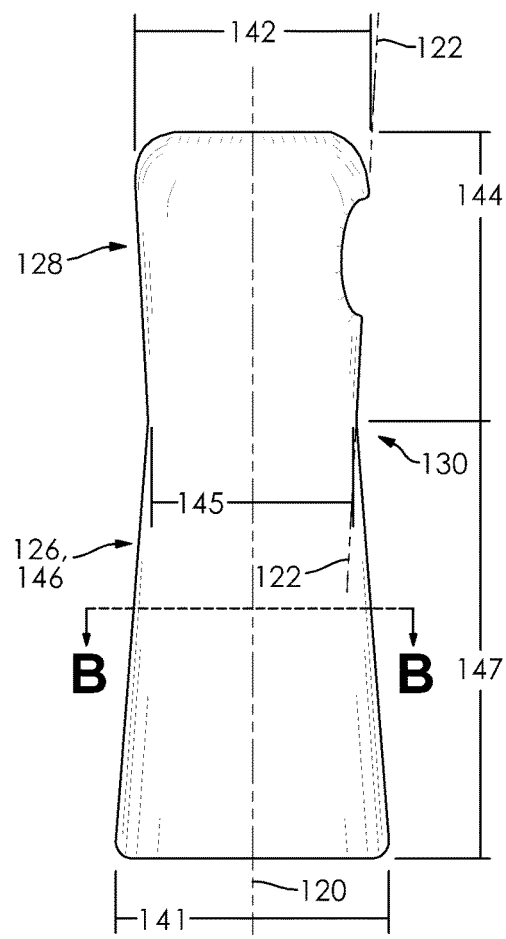
FIG. 11 is a bottom plan view of the pillow sleeve device shown in FIG. 9.
Figure 16:
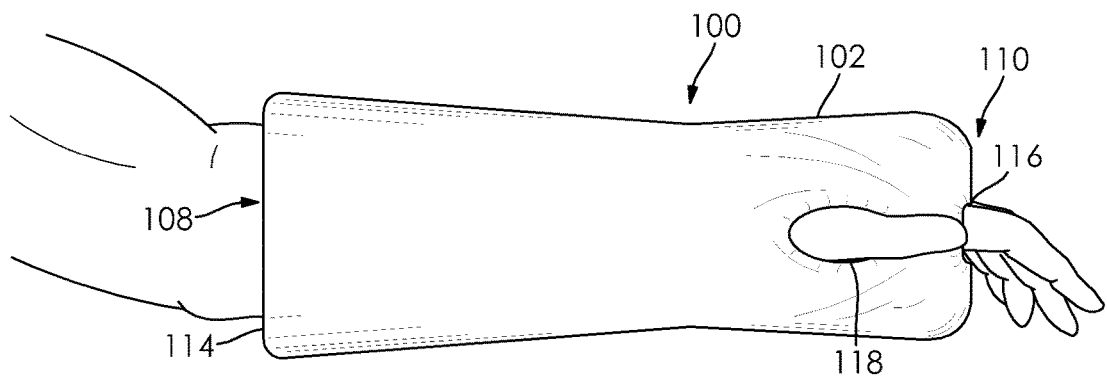
FIG. 16 is a top perspective view of the pillow sleeve device shown in FIG. 9, illustrated in use on the forearm and the hand of the user.
Figure 17:
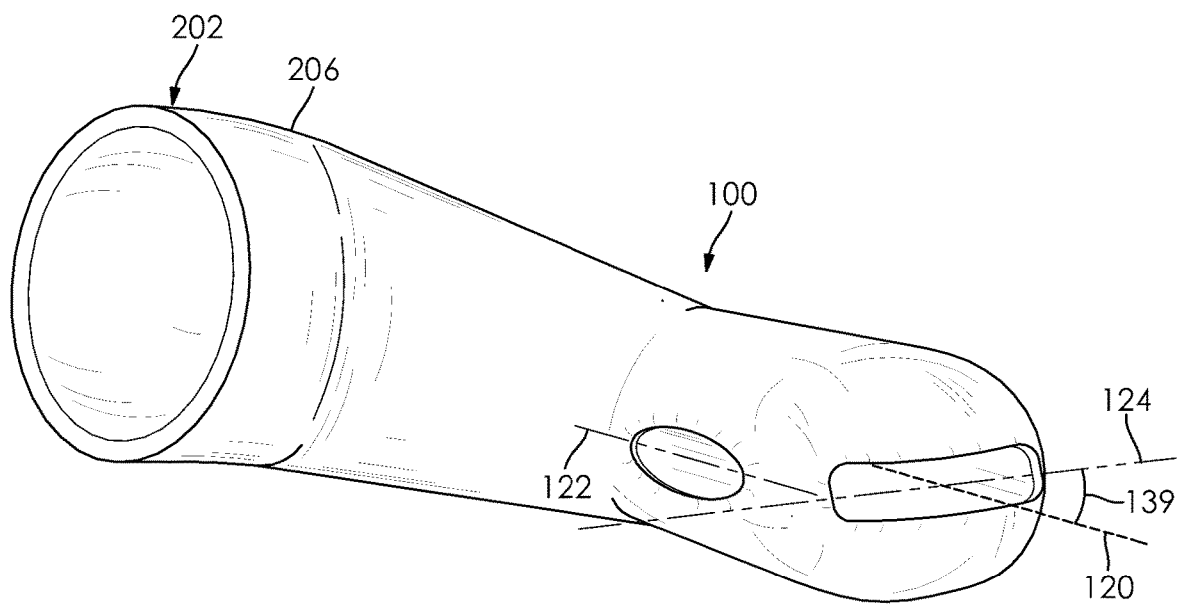
FIG. 17 is a top perspective view of a pillow sleeve device according to one embodiment of the present disclosure, the pillow sleeve device configured for placement on the forearm and the hand of the user and also for extending over an elbow of the user.

It should also be appreciated that the present disclosure also includes a resting or sleeping method 800, for example, as shown in FIG. 8. In some embodiments, at step 810, the resting or sleeping method 800 may include providing the pillow sleeve device. At step 820, the resting or sleeping method 800 may include selecting, by the user, either the right arm or the left arm on which to wear the pillow sleeve device. At step 830, the resting or sleeping method 800 may include disposing, by the user, the fingers of the hand through the fingers opening of the main body. At step 840, the resting or sleeping method 800 may include placing, by the user, the thumb of the hand through the thumb-opening of the main body. At step 850, the resting or sleeping method 800 may include resting, by the user, a head of the user on either the arm portion or the hand portion of the main body. Following the steps 810 to 850, the resting or sleeping method 800 may further include inserting, by the user, the hand and the arm of the user through the arm opening of the main body. The user may thereby be permitted to rest or sleep on the soft resting surface of the main body 102 of the pillow sleeve device 100 as provided.

EXAMPLES

Example embodiments of the present technology are provided with particular reference to the FIGS. 9-30 enclosed herewith.

With reference to FIGS. 9-15, a first example of the pillow sleeve device 100 is illustrated, where the pillow sleeve device 100 covers a major portion of the forearm of the user, but does not cover the elbow of the user.

A second example of the pillow sleeve device 100 is illustrated in FIGS. 16-24, where the pillow sleeve device 100 covers an entirety of the forearm of the user and also the elbow of the user, but does not cover a bicep of the user.

Referring to FIG. 25, a third example of the pillow sleeve device 100 is illustrated, where the pillow sleeve device 100 has the faux fur covering 308. The faux fur covering 308 may be permanently or removably attached to the main body 102, as desired.

A fourth example of the pillow sleeve device 100 is illustrated in FIG. 26, where the pillow sleeve device 100 has the branding area 400 containing the custom branding 402.

With reference to FIG. 27, a fifth example of the pillow sleeve device 100 is illustrated, where the pillow sleeve device 100 has the character or animal representation 300, and specifically a shark representation with eyes, a mouth, and fins.

A sixth example of the pillow sleeve device 100 is illustrated in FIG. 28, where the pillow sleeve device 100 has the electronics package 600, and specifically the visual unit 606, the auditory unit 610, and the user interface 616.

Referring now to FIG. 29, a seventh example of the pillow sleeve device 100 is shown in cross-section, where two layers of the at least one flexible shell 104 are shown encapsulating the at least one cushion fill 106.

An eighth example of the pillow sleeve device 100 is shown in cross-section in FIG. 30, where the at least one cushion fill 106 is shown disposed along an entire length of the pillow sleeve device 100.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well known processes, well known device structures, and well known technologies are not described in detail. Equivalent changes, modifications and variations of some embodiments, materials, compositions and methods can be made within the scope of the present technology, with substantially similar results.

What is claimed is:

1. A pillow sleeve device, comprising:
   a main body having at least one flexible shell and at least one cushion fill, the at least one flexible shell enveloping the at least one cushion fill, the at least one flexible shell and the at least one cushion fill together providing a soft resting surface for sleeping by a user,
   the main body being generally tubular with a first end, a second end, and a hollow passage, the hollow passage being elongate and arranged on a central axis of the main body,
   the main body having an arm portion and a hand portion, the arm portion configured to receive and be supported by at least part of an arm of the user, and the hand portion having configured to receive and be supported by at least part of a hand of the user,
   the arm portion disposed proximal the first end of the main body, and the hand portion disposed proximal the second end of the main body, the arm portion defining an arm opening configured to receive the hand and the arm during a wearing of the pillow sleeve device by the user, and the hand portion defining a fingers opening configured to receive fingers but not a thumb of the hand during the wearing of the pillow sleeve device by the user so that the fingers are exposed and not covered by the hand portion of the main body, the arm opening in communication with the fingers opening by the hollow passage of the main body, the fingers opening being elongate and arranged on a fingers opening axis, and the fingers opening being substantially rectangular in shape,
   the hand portion further having a thumb opening configured to receive only the thumb of the hand during the wearing of the pillow sleeve device by the user so that the thumb is exposed and not covered by the hand portion of the main body, and
   the thumb opening is elongate and arranged on a thumb opening axis spaced apart from and oriented substantially parallel with the central axis of the main body, the thumb opening configured to receive the thumb regardless of the thumb being on the hand of a right arm or a left arm of the user so that the pillow sleeve device is ambidextrous.

2. The pillow sleeve device of claim 1, wherein the arm portion includes a forearm portion that is configured receive and be supported by only a forearm of the user.

3. The pillow sleeve device of claim 2, wherein at least part of the forearm portion flares outwardly toward the first end of the main body, the at least part of the forearm portion having a flared forearm surface oriented on a forearm flare axis, the forearm flare axis arranged at a forearm flare angle relative to the central axis of the main body.

4. The pillow sleeve device of claim 2, wherein the main body further has a wrist portion, the wrist portion disposed between the arm portion and the hand portion of the main body.

5. The pillow sleeve device of claim 4, wherein the arm portion has a maximum arm portion exterior diameter, the hand portion has a maximum hand portion exterior diameter, and the wrist portion has a maximum wrist portion exterior diameter, the maximum wrist portion exterior diameter being less than the maximum hand portion exterior diameter.

6. The pillow sleeve device of claim 5, wherein the maximum arm portion exterior diameter is substantially equal to the maximum wrist portion exterior diameter, and at least part of the wrist portion flares outwardly toward the second end of the main body, the at least part of the wrist portion having a flared wrist surface oriented on a wrist flare axis, the wrist flare axis arranged at a wrist flare angle relative to the central axis of the main body.

7. The pillow sleeve device of claim 4, wherein the at least one flexible shell further has a pouch configured for receiving items to be held by the user, and the pouch is disposed on one of the arm portion, the wrist portion, and the hand portion.

8. The pillow sleeve device of claim 2, wherein the arm portion further includes an elbow portion configured to be received and supported by an elbow of the user, the forearm portion disposed between the elbow portion and the hand portion of the main body, and the elbow portion is arranged on an elbow portion axis, the elbow portion axis oriented at an elbow portion angle relative to the central axis of the main body.

9. The pillow sleeve device of claim 1, wherein the arm opening is substantially round in shape and arranged substantially coaxial with the central axis of the main body.

10. The pillow sleeve device of claim 1, wherein the at least one flexible shell is customizable with at least one decoration or decorative material.

11. The pillow sleeve device of claim 10, wherein the at least one decoration or decorative material is removably attached to the at least one flexible shell with at least one fastener.

12. The pillow sleeve device of claim 1, wherein the at least one flexible shell has a character or animal representation disposed on the hand portion.

13. The pillow sleeve device of claim 1, wherein the at least one flexible shell has a faux fur covering.

14. The pillow sleeve device of claim 1, wherein the at least one flexible shell has a branding area configured to receive a custom branding.

15. The pillow sleeve device of claim 1, wherein the at least one flexible shell further envelopes an electronics package, the electronics package including a power source, a controller, and at least one of a visual unit, an auditory unit, and a vibratory unit in communication with the power source and the controller.

16. The pillow sleeve device of claim 15, wherein at least one of the visual unit, the auditory unit, and the vibratory unit are configured to activate at a predetermined time by the controller and to operate as an alarm for the user when resting or sleeping.

17. The pillow sleeve device of claim 1, wherein the fingers opening axis is oriented at a fingers opening angle relative to the thumb opening axis, and the thumb opening has either an ovoid shape or a teardrop shape with a rounded forward section proximal to the fingers opening.

18. A method for manufacturing a pillow sleeve device, the method comprising steps of:
providing at least one flexible shell material and at least one cushion fill material;
measuring a forearm of a user to provide user measurements;
selecting an appropriate size for the pillow sleeve device based on the user measurements;
creating a sewing pattern with the user measurements;
applying the sewing pattern to the at least one flexible shell material according to the sewing pattern by either folding or cutting the at least one flexible shell material to provide at least one flexible shell with two layers of the at least one flexible shell material;
sewing the at least one flexible shell to provide an enveloping volume for filling with the at least one cushion fill material;
filling the enveloping volume of the at least one flexible shell with the at least one cushion fill material to provide at least one cushion fill; and
sewing ends of the at least one flexible shell to construct the pillow sleeve device, wherein the pillow sleeve device includes a main body having the at least one flexible shell and the at least one cushion fill, the at least one flexible shell enveloping the at least one cushion fill, the at least one flexible shell and the at least one cushion fill together providing a soft resting surface for sleeping by a user, the main body being generally tubular with a first end, a second end, and a hollow passage, the hollow passage being elongate and arranged on a central axis of the main body, the main body having an arm portion and a hand portion, the arm portion configured to receive and be supported by at least part of an arm of the user, and the hand portion having configured to receive and be supported by at least part of a hand of the user, the arm portion disposed proximal the first end of the main body, and the hand portion disposed proximal the second end of the main body, the arm portion defining an arm opening configured to receive the hand and the arm during a wearing of the pillow sleeve device by the user, and the hand portion defining a fingers opening configured to receive fingers but not a thumb of the hand during the wearing of the pillow sleeve device by the user so that the fingers are exposed and not covered by the hand portion of the main body, the arm opening in communication with the fingers opening by the hollow passage of the main body, the fingers opening being elongate and arranged on a fingers opening axis, and the fingers opening being substantially rectangular in shape, the hand portion further having a thumb opening configured to receive only the thumb of the hand during the wearing of the pillow sleeve device by the user so that the thumb is exposed and not covered by the hand portion of the main body, and the thumb opening is elongate and arranged on a thumb opening axis spaced apart from and oriented substantially parallel with the central axis of the main body, the thumb opening configured to receive the thumb regardless of the thumb being on the hand of a right arm or a left arm of the user so that the pillow sleeve device is ambidextrous.

19. A method for resting or sleeping, the method comprising steps of:
providing a pillow sleeve device, including a main body having at least one flexible shell and at least one cushion fill, the at least one flexible shell enveloping the at least one cushion fill, the at least one flexible shell and the at least one cushion fill together providing a soft resting surface for sleeping by a user, the main body being generally tubular with a first end, a second end, and a hollow passage, the hollow passage being elongate and arranged on a central axis of the main body, the main body having an arm portion and a hand portion, the arm portion configured to receive and be supported by at least part of an arm of the user, and the hand portion having configured to receive and be supported by at least part of a hand of the user, the arm portion disposed proximal the first end of the main body, and the hand portion disposed proximal the second end of the main body, the arm portion defining an arm opening configured to receive the hand and the arm during a wearing of the pillow sleeve device by the user, and the hand portion defining a fingers opening configured to receive fingers but not a thumb of the hand during the wearing of the pillow sleeve device by the user so that the fingers are exposed and not covered by the hand portion of the main body, the arm opening in communication with the fingers opening by the hollow passage of the main body, the fingers opening being elongate and arranged on a fingers opening axis, and the fingers opening being substantially rectangular in shape, the hand portion further having a thumb opening configured to receive only the thumb of the hand during the wearing of the pillow sleeve device by the user so that the thumb is exposed and not covered by the hand portion of the main body, and the thumb opening is elongate and arranged on a thumb opening axis spaced apart from and oriented substantially parallel with the central axis of the main body, the thumb opening configured to receive the thumb regardless of the thumb being on the hand of a right arm or a left arm of the user so that the pillow sleeve device is ambidextrous;

selecting, by the user, either the right arm or the left arm on which to wear the pillow sleeve device;

inserting, by the user, the hand and the arm of the user through the arm opening of the main body;

inserting, by the user, the fingers of the hand through the fingers opening of the main body;

inserting, by the user, the thumb of the hand through the thumb opening of the main body;

resting, by the user, a head of the user on either the arm portion or the hand portion of the main body, and whereby the user is permitted to rest or sleep on the soft resting surface of the main body.

* * * * *